(12) United States Patent
Surleraux et al.

(10) Patent No.: US 7,595,334 B2
(45) Date of Patent: Sep. 29, 2009

(54) BROADSPECTRUM 2-(SUBSTITUTED-AMINO)-BENZOXAZOLE SULFONAMIDE HIV PROTEASE INHIBITORS

(75) Inventors: Dominique Louis Nestor Ghislain Surleraux, Machelen (BE); Sandrine Marie Helene Vendeville, Brussels (BE); Wim Gaston Verschueren, Berchem (BE); Marie-Pierre T. M. M. G. De Bethune, Everberg (BE); Herman Augustinus De Kock, Arendonk (BE); Abdellah Tahri, Heverlee (BE); Montserrat Erra Solà, Brussels (BE)

(73) Assignee: Tibotec Pharmaceuticals Ltd., Littl Island, Co.Cork (IE)

( * ) Notice: Subject to any disclaimer, the term of this patent is extended or adjusted under 35 U.S.C. 154(b) by 153 days.

(21) Appl. No.: 11/626,183

(22) Filed: Jan. 23, 2007

(65) Prior Publication Data

US 2007/0135447 A1  Jun. 14, 2007

Related U.S. Application Data

(62) Division of application No. 10/474,162, filed on Feb. 7, 2003, now Pat. No. 7,244,752.

(60) Provisional application No. 60/287,704, filed on Apr. 9, 2001.

(51) Int. Cl.
*A61K 31/421* (2006.01)
*A61K 31/426* (2006.01)
*C07D 263/54* (2006.01)
*C07D 277/02* (2006.01)
*C07D 413/02* (2006.01)

(52) U.S. Cl. .................. 514/374; 546/268.1; 546/269.7; 548/146; 548/215; 514/336; 514/365

(58) Field of Classification Search .................. 548/146, 548/203, 215; 546/268.1, 269.7; 514/336, 514/339, 365, 374, 377
See application file for complete search history.

(56) References Cited

U.S. PATENT DOCUMENTS

| | | | |
|---|---|---|---|
| 4,448,192 A | 5/1984 | Stawitcke et al. | |
| 4,844,085 A | 7/1989 | Gattinoni | |
| 5,136,043 A | 8/1992 | Meier et al. | |
| 5,756,533 A * | 5/1998 | Getman et al. | 514/422 |
| 7,244,752 B2 * | 7/2007 | Surleraux et al. | 514/365 |

FOREIGN PATENT DOCUMENTS

| | | | |
|---|---|---|---|
| EP | 0403947 A2 | 12/1990 | |
| EP | 0445926 A2 | 9/1991 | |
| EP | 0499299 A2 | 8/1992 | |
| EP | 0403947 B1 | 7/1994 | |
| EP | 0721331 B1 | 7/1996 | |
| EP | 0445926 B1 | 8/1996 | |
| EP | 0 885 887 A2 | 12/1998 | |
| EP | 0499299 B1 | 8/2000 | |
| EP | 0 885 887 B1 | 5/2003 | |
| GB | 2 077 444 A | 12/1981 | |

(Continued)

OTHER PUBLICATIONS

Goodman, et al., "Biotransformation of Drugs", The Pharmacological Basis of Therapeutics, p. 13-18, 8$^{th}$ Edition, 1990.

(Continued)

*Primary Examiner*—Golam M Shameem

(57) ABSTRACT

The present invention concerns the compounds having the formula (I)

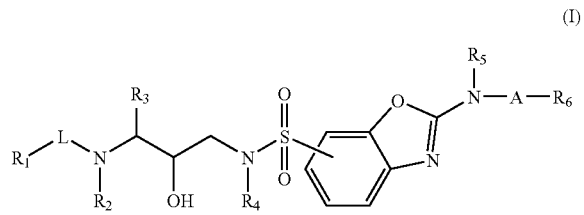

N-oxides, salts, stereoisomeric forms, racemic mixtures, prodrugs, esters and metabolites thereof, wherein $R_1$ and $R_8$ each are H, optionally substituted $C_{1-6}$alkyl, $C_{2-6}$alkenyl, $C_{3-7}$cycloalkyl, aryl, $Het^1$, $Het^2$; $R_1$ may also be a radical of formula $(R_{11a}R_{11b})NC(R_{10a}R_{10b})CR_9$—; t is 0, 1 or 2; $R_2$ is H or $C_{1-6}$alkyl; L is —C(=O)—, —O—C(=O)—, —$NR_8$—C(=O)—, —O—$C_{1-6}$alkanediyl-C(=O)—, —$NR_8$—$C_{1-6}$alkanediyl-C(=O)—, —S(=O)$_2$—, —O—S(=O)$_2$—, —$NR_8$—S(=O)$_2$; $R_3$ is $C_{1-6}$alkyl, aryl, $C_{3-7}$cycloalkyl, $C_{3-7}$cycloalkyl$C_{1-4}$alkyl, or aryl$C_{1-4}$alkyl; $R_4$ is H, $C_{1-4}$alkylOC(=O), carboxyl, aminoC(=O), mono- or di(C$_{1-4}$alkyl)aminoC(=O), $C_{3-7}$cycloalkyl, $C_{2-6}$alkenyl, $C_{2-6}$alkynyl or optionally substituted $C_{1-6}$alkyl; A is $C_{1-6}$alkanediyl, —C(=O)—, —C(=S)—, —S(=O)$_2$—, $C_{1-6}$alkanediyl-C(=O)—, $C_{1-6}$alkanediyl-C(=S)— or $C_{1-6}$alkanediyl-S(=O)$_2$—; $R_5$ is H, OH, $C_{1-6}$alkyl, $Het^1C_{1-6}$alkyl, $Het^2C_{1-6}$alkyl, optionally substituted amino$C_{1-6}$alkyl; $R_6$ is $C_{1-6}$alkylO, $Het^1$, $Het^1O$, $Het^2$, $Het^2O$, aryl, arylO, $C_{1-6}$alkyloxycarbonylamino or amino; and in case -A- is other than $C_{1-6}$alkanediyl then $R_6$ may also be $C_{1-6}$alkyl, $Het^1C_{1-4}$alkyl, $Het^1OC_{1-4}$alkyl, $Het^2C_{1-4}$alkyl, $Het^2OC_{1-4}$alkyl, aryl $C_{1-4}$alkyl, arylO$C_{1-4}$alkyl or amino$C_{1-4}$alkyl; whereby each of the amino groups in the definition of $R_6$ may optionally be substituted; -A-$R_6$ is hydroxy$C_{1-6}$alkyl; $R_5$ and -A-$R_6$ taken together with the nitrogen atom to which they are attached may also form $Het^1$ or $Het^2$. It further relates to their use as broadspectrum HIV protease inhibitors, processes for their preparation as well as pharmaceutical compositions and diagnostic kits comprising them. It also concerns combinations thereof with another anti-retroviral agent, and to their use in assays as reference compounds or as reagents.

17 Claims, No Drawings

FOREIGN PATENT DOCUMENTS

| | | |
|---|---|---|
| WO | WO 94/05263 A1 | 3/1994 |
| WO | WO 95/06030 A1 | 3/1995 |
| WO | WO 95/14653 A1 | 6/1995 |
| WO | WO 95/09615 A1 | 4/1996 |
| WO | WO 96/22287 A1 | 7/1996 |
| WO | WO 96/28418 A1 | 9/1996 |
| WO | WO 96/28463 A1 | 9/1996 |
| WO | WO 96/28464 A1 | 9/1996 |
| WO | WO 96/28465 A1 | 9/1996 |
| WO | WO 97/18205 A1 | 5/1997 |
| WO | WO 97/22377 A1 | 6/1997 |
| WO | WO 97/44014 A1 | 11/1997 |
| WO | WO 98/42318 A1 | 10/1998 |
| WO | WO 99/33792 A2 | 7/1999 |
| WO | WO 99/33793 A2 | 7/1999 |
| WO | WO 99/33795 A1 | 7/1999 |
| WO | WO 99/33815 A1 | 7/1999 |
| WO | WO 99/67254 A2 | 12/1999 |
| WO | WO 99/67417 A2 | 12/1999 |
| WO | WO 01/25240 A1 | 4/2001 |

OTHER PUBLICATIONS

Hertogs, et al., "A Rapid Method for Simultaneous Detection of Phenotypic Resistance to Inhibitors of Protease and Reverse Transcriptase in Recombinant Human Immunodeficiency Virus Type 1 Isolates from Patients Treated with Antiretroviral Drugs", Antimicrobial Agents and Chemotherapy, vol. 42, (1998) pp. 269-276.

Augustijns, et al., "Drug absorption studies of prodrug esters using the Caco-2 model: evaluation of ester hydrolysis and transepithelial transport", International Journal of Pharmaceutics 166, (1998) pp. 44-54.

International Search Report re: PCT/EP02/004012, dated Dec. 17, 2002.

* cited by examiner

BROADSPECTRUM 2-(SUBSTITUTED-AMINO)-BENZOXAZOLE SULFONAMIDE HIV PROTEASE INHIBITORS

CROSS REFERENCE TO RELATED APPLICATIONS

This Application is a divisional of U.S. application for patent Ser. No. 10/474,162, filed Feb. 7, 2003, now U.S. Pat. No. 7,244,752 which is the National Stage Application under 35 U.S.C. § 371 of PCT/EP02/04012, filed Apr. 9, 2002, which claims priority to U.S. Provisional Application Ser. No. 60/287,704, filed May 2, 2001, and to European patent application EP 01201308.2, filed on Apr. 9, 2001, all of which are incorporated herein by reference in their entirety.

The present invention relates to 2-(substituted-amino)-benzoxazole sulfonamides, their use as aspartic protease inhibitors, in particular as broadspectrum HIV protease inhibitors, processes for their preparation as well as pharmaceutical compositions and diagnostic kits comprising them. The present invention also concerns combinations of the present 2-(substituted-amino)-benzoxazole sulfonamides with another anti-retroviral agent. It further relates to their use in assays as reference compounds or as reagents.

The virus causing the acquired immunodeficiency syndrome (AIDS) is known by different names, including T-lymphocyte virus III (HTLV-III) or lymphadenopathy-associated virus (LAV) or AIDS-related virus (ARV) or human immunodeficiency virus (HIV). Up until now, two distinct families have been identified, i.e. HIV-1 and HIV-2. Hereinafter, HIV will be used to generically denote these viruses.

One of the critical pathways in a retroviral life cycle is the processing of polyprotein precursors by aspartic protease. For instance with the HIV virus the gag-pol protein is processed by HIV protease. The correct processing of the precursor polyproteins by the aspartic protease is required for the assembly of infectious virions, thus making the aspartic protease an attractive target for antiviral therapy. In particular for HIV treatment, the HIV protease is an attractive target.

HIV protease inhibitors (PIs) are commonly administered to AIDS patients in combination with other anti-HIV compounds such as, for instance nucleoside reverse transcriptase inhibitors (NRTIs), non-nucleoside reverse transcriptase inhibitors (NNRTIs), nucleotide reverse transcriptase inhibitors (NtRTIs) or other protease inhibitors. Despite the fact that these antiretrovirals are very useful, they have a common limitation, namely, the targeted enzymes in the HIV virus are able to mutate in such a way that the known drugs become less effective, or even ineffective against these mutant HIV viruses. Or, in other words, the HIV virus creates an ever increasing resistance against the available drugs.

Resistance of retroviruses, and in particular the HIV virus, against inhibitors is a major cause of therapy failure. For instance, half of the patients receiving anti-HIV combination therapy do not respond fully to the treatment, mainly because of resistance of the virus to one or more drugs used. Moreover, it has been shown that resistant virus is carried over to newly infected individuals, resulting in severely limited therapy options for these drug-naive patients. Therefore, there is a need in the art for new compounds for retrovirus therapy, more particularly for AIDS therapy. The need in the art is particularly acute for compounds that are active not only on wild type HIV virus, but also on the increasingly more common resistant HIV viruses.

Known antiretrovirals, often administered in a combination therapy regimen, will eventually cause resistance as stated above. This often may force the physician to boost the plasma levels of the active drugs in order for said antiretrovirals to regain effectivity against the mutated HIV viruses. The consequence of which is a highly undesirable increase in pill burden. Boosting plasma levels may also lead to an increased risk of non-compliance with the prescribed therapy. Thus, it is not only important to have compounds showing activity for a wide range of HIV mutants, it is also important that there is little or no variance in the ratio between activity against mutant HIV virus and activity against wild type HIV virus (also defined as fold resistance or FR) over a broad range of mutant HIV strains. As such, a patient may remain on the same combination therapy regimen for a longer period of time since the chance that a mutant HIV virus will be sensitive to the active ingredients will be increased.

Finding compounds with a high potency on the wild type and on a wide variety of mutants is also of importance since the pill burden can be reduced if therapeutic levels are kept to a minimum. One way of reducing this pill burden is finding anti-HIV compounds with good bioavailability, i.e. a favorable pharmacokinetic and metabolic profile, such that the daily dose can be minimized and consequently also the number of pills to be taken.

Another important characteristic of a good anti-HIV compound is that plasma protein binding of the inhibitor has minimal or even no effect on its potency.

Thus, there is a high medical need for protease inhibitors that are able to combat a broad spectrum of mutants of the HIV virus with little variance in fold resistance, have a good bioavailability and experience little or no effect on their potency due to plasma protein binding.

Up until now, several protease inhibitors are on the market or are being developed. One particular core structure (depicted below) has been disclosed in a number of references, such as, WO 95/06030, WO 96/22287, WO 96/28418, WO 96/28463, WO 96/28464, WO 96/28465 and WO 97/18205. The compounds disclosed therein are described as retroviral protease inhibitors.

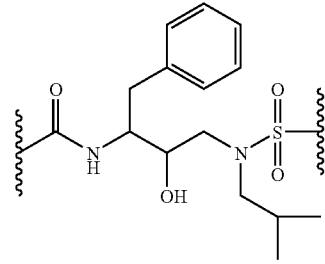

WO 99/67254 discloses 4-substituted-phenyl sulfonamides capable of inhibiting multi-drug resistant retroviral proteases.

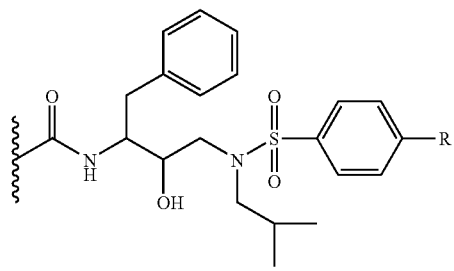

Surprisingly, the 2-(substituted-amino)-benzoxazole sulfonamides of the present invention are found to have a favorable pharmacological and pharmacokinetic profile. Not only are they active against wild-type HIV virus, but they also show a broadspectrum activity against various mutant HIV viruses exhibiting resistance against known protease inhibitors.

The present invention concerns 2-(substituted-amino)-benzoxazole protease inhibitors, having the formula

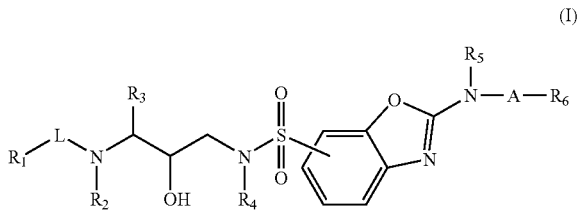

(I)

and N-oxides, salts, stereoisomeric forms, racemic mixtures, prodrugs, esters and metabolites thereof, wherein $R_1$ and $R_8$ are, each independently, hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, Het$^1$, Het$^1C_{1-6}$alkyl, Het$^2$, Het$^2$ $C_{1-6}$alkyl;

$R_1$ may also be a radical of formula

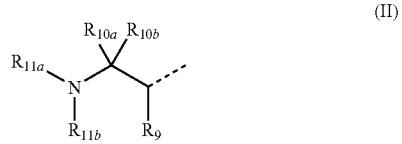

(II)

wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, Het$^1$, Het$^2$, $C_{3-7}$cycloalkyl, $C_{1-4}$alkyloxycarbonyl, carboxyl, aminocarbonyl, mono- or di($C_{1-4}$alkyl) aminocarbonyl, aminosulfonyl, $C_{1-4}$alkylS(O)$_t$, hydroxy, cyano, halogen or amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl; whereby $R_9$, $R_{10a}$ and the carbon atoms to which they are attached may also form a $C_{3-7}$cycloalkyl radical; when L is —O—$C_{1-6}$alkanediyl-C(=O)— or —NR$_8$-$C_{1-6}$alkanediyl-C (=O)—, then $R_9$ may also be oxo;

$R_{11a}$ is hydrogen, $C_{2-6}$alkenyl, $C_{2-6}$alkynyl, $C_{3-7}$cycloalkyl, aryl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, Het$^1$oxy-carbonyl, Het$^2$oxycarbonyl, aryloxycarbonyl$C_{1-4}$alkyl, aryl$C_{1-4}$alkyloxy-carbonyl, $C_{1-4}$alkylcarbonyl, $C_{3-7}$cycloalkylcarbonyl, $C_{3-7}$cycloalkyl-$C_{1-4}$alkyloxycarbonyl, $C_{3-7}$cycloalkylcarbonyloxy, carboxyl$C_{1-4}$alkyl-carbonyloxy, $C_{1-4}$alkylcarbonyloxy, aryl$C_{1-4}$alkylcarbonyloxy, arylcarbonyloxy, aryloxycarbonyloxy, Het$^1$carbonyl, Het$^1$carbonyloxy, Het$^1C_{1-4}$alkyloxycarbonyl, Het$^2$carbonyloxy, Het$^2$ $C_{1-4}$alkylcarbonyloxy, Het$^2C_{1-4}$alkyloxycarbonyloxy or $C_{1-4}$alkyl optionally substituted with aryl, aryloxy, Het$^2$, halogen or hydroxy; wherein the substituents on the amino groups are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

$R_{11b}$ is hydrogen, $C_{3-7}$cycloalkyl, $C_{2-6}$alkenyl, $C_{2-6}$alkynyl, aryl, Het$^1$, Het$^2$ or $C_{1-4}$alkyl optionally substituted with halogen, hydroxy, $C_{1-4}$alkylS(=O)$_t$, aryl, $C_{3-7}$cycloalkyl, Het$^1$, Het$^2$, amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1$ $C_{1-4}$alkyl and Het$^2C_{1-4}$alkyl;

whereby $R_{11b}$ may be linked to the remainder of the molecule via a sulfonyl group;

each independently, t is zero, 1 or 2;

$R_2$ is hydrogen or $C_{1-6}$alkyl;

L is —C(=O)—, —O—C(=O)—, —NR$_8$—C(=O)—, —O—$C_{1-6}$alkanediyl-C(=O)—, —NR$_8$—$C_{1-6}$alkanediyl-C(=O)—, —S(=O)$_2$—, —O—S(=O)$_2$—, —NR$_8$—S(=O)$_2$ whereby either the C(=O) group or the S(=O)$_2$ group is attached to the NR$_2$ moiety; whereby the $C_{1-6}$alkanediyl moiety is optionally substituted with aryl, Het$^1$, Het$^2$;

$R_3$ is $C_{1-6}$alkyl, aryl, $C_{3-7}$cycloalkyl, $C_{3-7}$cycloalkyl$C_{1-4}$alkyl, or aryl$C_{1-4}$alkyl;

$R_4$ is hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl, or $C_{1-6}$alkyl optionally substituted with one or more substituents each independently selected from aryl, Het$^1$, Het$^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(=O)$_t$, hydroxy, cyano, halogen and amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1C_{1-4}$alkyl and Het$^2C_{1-4}$alkyl;

A is $C_{1-6}$alkanediyl, —C(=O)—, —C(=S)—, —S(=O)$_2$—, $C_{1-6}$alkanediyl-C(=O)—, $C_{1-6}$alkane-diyl-C(=S)— or $C_{1-6}$alkanediyl-S(=O)$_2$—; whereby the point of attachment to the nitrogen atom is the $C_{1-6}$alkanediyl group in those moieties containing said group;

$R_5$ is hydrogen, hydroxy, $C_{1-6}$alkyl, Het$^1C_{1-6}$alkyl, Het$^2$ $C_{1-6}$alkyl, amino$C_{1-6}$alkyl whereby the amino group may optionally be mono- or di-substituted with $C_{1-4}$alkyl;

$R_6$ is $C_{1-6}$alkyloxy, Het$^1$, Het$^1$oxy, Het$^2$, Het$^2$oxy, aryl, aryloxy or amino; and in case -A- is other than $C_{1-6}$alkanediyl then $R_6$ may also be $C_{1-6}$alkyl, Het$^1C_{1-4}$alkyl, Het$^1$oxy $C_{1-4}$alkyl, Het$^2C_{1-4}$alkyl, Het$^2$oxy$C_{1-4}$alkyl, aryl$C_{1-4}$alkyl, aryloxy$C_{1-4}$alkyl or amino$C_{1-6}$alkyl; whereby each of the amino groups in the definition of $R_6$ may optionally be substituted with one or more substituents each independently selected from $C_{1-4}$alkyl, $C_{1-4}$alkylcarbonyl, $C_{1-4}$alkyloxycarbonyl, aryl, arylcarbonyl, aryloxycarbonyl, Het$^1$, Het$^2$, aryl$C_{1-4}$alkyl, Het$^1C_{1-4}$alkyl or Het$^2$ $C_{1-4}$alkyl; and -A-$R_6$ may also be hydroxy$C_{1-6}$alkyl;

$R_5$ and -A-$R_6$ taken together with the nitrogen atom to which they are attached may also form Het$^1$ or Het$^2$.

This invention also envisions the quaternization of the nitrogen atoms of the present compounds. A basic nitrogen can be quaternized with any agent known to those of ordinary skill in the art including, for instance, lower alkyl halides, dialkyl sulfates, long chain halides and aralkyl halides.

Whenever the term "substituted" is used in defining the compounds of formula (I), it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic agent.

As used herein, the term "halo" or "halogen" as a group or part of a group is generic for fluoro, chloro, bromo or iodo.

The term "$C_{1-4}$alkyl" as a group or part of a group defines straight and branched chained saturated hydrocarbon radicals having from 1 to 4 carbon atoms, such as, for example, methyl, ethyl, propyl, butyl and 2-methyl-propyl, and the like.

The term "$C_{1-6}$alkyl" as a group or part of a group defines straight and branched chained saturated hydrocarbon radicals having from 1 to 6 carbon atoms such as the groups defined for $C_{1-4}$alkyl and pentyl, hexyl, 2-methylbutyl, 3-methylpentyl and the like.

The term "$C_{1-6}$alkanediyl" as a group or part of a group defines bivalent straight and branched chained saturated hydrocarbon radicals having from 1 to 6 carbon atoms such as, for example, methylene, ethan-1,2-diyl, propan-1,3-diyl, propan-1,2-diyl, butan-1,4-diyl, pentan-1,5-diyl, hexan-1,6-diyl, 2-methylbutan-1,4-diyl, 3-methylpentan-1,5-diyl and the like.

The term "$C_{2-6}$alkenyl" as a group or part of a group defines straight and branched chained hydrocarbon radicals having from 2 to 6 carbon atoms containing at least one double bond such as, for example, ethenyl, propenyl, butenyl, pentenyl, hexenyl and the like.

The term "$C_{2-6}$alkynyl" as a group or part of a group defines straight and branched chained hydrocarbon radicals having from 2 to 6 carbon atoms containing at least one triple bond such as, for example, ethynyl, propynyl, butynyl, pentynyl, hexynyl and the like.

The term "$C_{3-7}$cycloalkyl" as a group or part of a group is generic to cyclopropyl, cyclobutyl, cyclopentyl, cyclohexyl or cycloheptyl.

The term "aryl" as a group or part of a group is meant to include phenyl and naphtyl which both may be optionally substituted with one or more substituents independently selected from $C_{1-6}$alkyl, optionally mono- or disubstituted amino$C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, methylthio, methylsulfonyl, and phenyl optionally substituted with one or more substituents each independently selected from $C_{1-6}$alkyl, optionally mono- or disubstituted amino$C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, methylthio and methylsulfonyl; whereby the optional substituents on any amino function are independently selected from $C_{1-6}$alkyl, optionally mono- or disubstituted amino$C_{1-6}$alkyl, $C_{1-6}$alkyloxy-A-, Het$^1$-A-, Het$^1$C$_{1-6}$alkyl, Het$^1$C$_{1-6}$alkyl-A-, Het$^1$oxy-A-, Het$^1$oxy C$_{1-4}$akyl-A-, phenyl-A-, phenyl-oxy-A-, phenyloxy C$_{1-4}$alkyl-A-, phenyl-C$_{1-6}$alkyl-A-, C$_{1-6}$alkyloxycarbonylamino-A-, amino-A-, amino$C_{1-6}$alkyl and amino-$C_{1-6}$alkyl-A- whereby each of the amino groups may optionally be mono- or where possible di-substituted with $C_{1-4}$alkyl and whereby A is as defined above.

An interesting subgroup in the definition of "aryl" as a group or part of a group includes phenyl and naphtyl which both may be optionally substituted with one or more substituents independently selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, methylthio, methylsulfonyl, and phenyl optionally substituted with one or more substituents selected from $C_{1-6}$alkyl, $C_{1-6}$alkyloxy, halogen, hydroxy, optionally mono- or disubstituted amino, nitro, cyano, halo$C_{1-6}$alkyl, carboxyl, $C_{1-6}$alkoxycarbonyl, $C_{3-7}$cycloalkyl, Het$^1$, optionally mono- or disubstituted aminocarbonyl, methylthio and methylsulfonyl; whereby the optional substituents on any amino function are independently selected from $C_{1-6}$alkyl, $C_{1-6}$alkyloxy-A-, Het$^1$-A-, Het$^1$C$_{1-6}$alkyl, Het$^1$C$_{1-6}$alkyl-A-, Het$^1$oxy-A-, Het$^1$oxyC$_{1-4}$akyl-A-, phenyl-A-, phenyl-oxy-A-, phenyloxyC$_{1-4}$alkyl-A-, phenylC$_{1-6}$alkyl-A-, C$_{1-6}$alkyloxycarbonyl-amino-A-, amino-A-, amino$C_{1-6}$alkyl and amino $C_{1-6}$alkyl-A- whereby each of the amino groups may optionally be mono- or where possible di-substituted with $C_{1-4}$alkyl and whereby A is as defined above, The term "halo$C_{1-6}$alkyl" as a group or part of a group is defined as $C_{1-6}$alkyl substituted with one or more halogen atoms, preferably, chloro or fluoro atoms, more preferably fluoro atoms. Preferred halo$C_{1-6}$alkyl groups include for instance trifluoromethyl and difluoromethyl.

The term "Het$^1$" as a group or part of a group is defined as a saturated or partially unsaturated monocyclic, bicyclic or tricyclic heterocycle having preferably 3 to 14 ring members, more preferably 5 to 10 ring members and more preferably 5 to 8 ring members, which contains one or more heteroatom ring members each independently selected from nitrogen, oxygen or sulfur and which is optionally substituted on one or more carbon atoms by $C_{1-6}$alkyl, optionally mono- or disubstituted amino$C_{1-6}$alkyl, $C_{1-6}$alkyloxy, halogen, hydroxy, oxo, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 14 ring members which contains one or more heteroatom ring members each independently selected from nitrogen, oxygen or sulfur and whereby the optional substituents on any amino function are independently selected from $C_{1-6}$alkyl, optionally mono- or disubstituted amino$C_{1-6}$alkyl, $C_{1-6}$alkyloxy-A-, Het$^2$-A-, Het$^2$C$_{1-6}$alkyl, Het$^2$C$_{1-6}$alkyl-A-, Het$^2$oxy-A-, Het$^2$oxyC$_{1-4}$akyl-A-, aryl-A-, aryloxy-A-, aryloxyC$_{1-4}$alkyl-A-, arylC$_{1-6}$alkyl-A-, C$_{1-6}$alkyloxycarbonylamino-A-, amino-A-, amino$C_{1-6}$alkyl and amino$C_{1-6}$alkyl-A- whereby each of the amino groups may optionally be mono- or where possible di-substituted with $C_{1-4}$alkyl and whereby A is as defined above. An interesting subgroup in the definition of "Het$^1$" as a group or part of a group is defined as a saturated or partially unsaturated monocyclic, bicyclic or tricyclic heterocycle having preferably 3 to 12 ring members, more preferably 5 to 10 ring members and more preferably 5 to 8 ring members, which contains one or more heteroatom ring members selected from nitrogen, oxygen or sulfur and which is optionally substituted on one or more carbon atoms by $C_{1-6}$alkyl, $C_{1-6}$alkyloxy, halogen, hydroxy, oxo, optionally mono- or disubstituted amino, nitro, cyano, halo$C_{1-6}$alkyl, carboxyl, $C_{1-6}$alkoxycarbonyl, $C_{3-7}$cycloalkyl, optionally mono- or disubstituted aminocarbonyl, methylthio, methylsulfonyl, aryl and a saturated or partially unsaturated monocyclic, bicyclic or tricyclic heterocycle having 3 to 12 ring members which contains one or more heteroatom ring members selected from nitrogen, oxygen or sulfur and whereby the optional substituents on any amino function are independently selected from $C_{1-6}$alkyl, $C_{1-6}$alkyloxy-A-, Het$^2$-A-, Het$^2$C$_{1-6}$alkyl, Het$^2$C$_{1-6}$alkyl-A-, Het$^2$oxy-A-, Het$^2$oxy C$_{1-4}$akyl-A-, aryl-A-, aryloxy-A-, aryloxyC$_{1-4}$alkyl-A-, arylC$_{1-6}$alkyl-A-, C$_{1-6}$alkyloxycarbonylamino-A-, amino- A-, aminoC$_{1-6}$alkyl and aminoC$_{1-6}$alkyl-A- whereby each of the amino groups may optionally be mono- or where possible di-substituted with C$_{1-4}$alkyl and whereby A is as defined above.

The term "Het$^2$" as a group or part of a group is defined as an aromatic monocyclic, bicyclic or tricyclic heterocycle having preferably 3 to 14 ring members, more preferably 5 to 10 ring members and more preferably 5 to 6 ring members, which contains one or more heteroatom ring members each independently selected from nitrogen, oxygen or sulfur and which is optionally substituted on one or more carbon atoms by C$_{1-6}$alkyl, optionally mono- or disubstituted amino C$_{1-6}$alkyl, C$_{1-6}$alkyloxy, halogen, hydroxy, optionally mono- or disubstituted amino, nitro, cyano, haloC$_{1-6}$alkyl, carboxyl, C$_{1-6}$alkoxycarbonyl, C$_{3-7}$cycloalkyl, optionally mono- or disubstituted aminocarbonyl, methylthio, methylsulfonyl, aryl, Het$^1$ and an aromatic monocyclic, bicyclic or tricyclic heterocycle having 3 to 14 ring members; whereby the optional substituents on any amino function are independently selected from C$_{1-6}$alkyl, optionally mono- or disubstituted aminoC$_{1-6}$alkyl, C$_{1-6}$alkyloxy-A-, Het$^1$-A-, Het$^1$C$_{1-6}$alkyl, Het$^1$C$_{1-6}$alkyl-A-, Het$^1$oxy-A-, Het$^1$oxyC$_{1-4}$akyl-A-, aryl-A-, aryloxy-A-, aryloxyC$_{1-4}$alkyl-A-, arylC$_{1-6}$alkyl-A-, C$_{1-6}$alkyloxycarbonylamino-A-, amino-A-, aminoC$_{1-6}$alkyl and aminoC$_{1-6}$alkyl-A- whereby each of the amino groups may optionally be mono- or where possible di-substituted with C$_{1-4}$alkyl and whereby A is as defined above.

An interesting subgroup in the definition of "Het$^2$" as a group or part of a group is defined as an aromatic monocyclic, bicyclic or tricyclic heterocycle having preferably 3 to 12 ring members, more preferably 5 to 10 ring members and more preferably 5 to 6 ring members, which contains one or more heteroatom ring members selected from nitrogen, oxygen or sulfur and which is optionally substituted on one or more carbon atoms by C$_{1-6}$alkyl, C$_{1-6}$alkyloxy, halogen, hydroxy, optionally mono- or disubstituted amino, nitro, cyano, haloC$_{1-6}$alkyl, carboxyl, C$_{1-6}$alkoxycarbonyl, C$_{3-7}$cycloalkyl, optionally mono- or disubstituted aminocarbonyl, methylthio, methylsulfonyl, aryl, Het$^1$ and an aromatic monocyclic, bicyclic or tricyclic heterocycle having 3 to 12 ring members; whereby the optional substituents on any amino function are independently selected from C$_{1-6}$alkyl, C$_{1-6}$alkyloxy-A-, Het$^1$-A-, Het$^1$C$_{1-6}$alkyl, Het$^1$C$_{1-6}$alkyl-A-, Het$^1$oxy-A-, Het$^1$oxyC$_{1-4}$akyl-A-, aryl-A-, aryloxy-A-, aryloxyC$_{1-4}$alkyl-A-, arylC$_{1-6}$alkyl-A-, C$_{1-6}$alkyloxycarbonylamino-A-, amino-A-, aminoC$_{1-6}$alkyl and aminoC$_{1-6}$alkyl-A- whereby each of the amino groups may optionally be mono- or where possible di-substituted with C$_{1-4}$alkyl and whereby A is as defined above.

As used herein, the term (=O) forms a carbonyl moiety with the carbon atom to which it is attached. The term (=O) forms a sulfoxide with the sulfur to which it is attached. The term (=O)$_2$ forms a sulfonyl to the sulfur to which it is attached.

As used herein, the term (=S) forms a thiocarbonyl moiety with the carbon atom to which it is attached.

As used herein before, the term "one or more" covers the possibility of all the available C-atoms, where appropriate, to be substituted, preferably, one, two or three.

When any variable (e.g. halogen or C$_{1-4}$alkyl) occurs more than one time in any constituent, each definition is independent.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs of a compound of the present invention are prepared by modifying functional groups present in the compound in such a way that the modifications are cleaved, either in routine manipulation or in vivo, to the parent compound. Prodrugs include compounds of the present invention wherein a hydroxy group, for instance the hydroxy group on the asymmetric carbon atom, or an amino group is bonded to any group that, when the prodrug is administered to a patient, cleaves to form a free hydroxyl or free amino, respectively.

Typical examples of prodrugs are described for instance in WO 99/33795, WO 99/33815, WO 99/33793 and WO 99/33792 all incorporated herein by reference.

Prodrugs are characterized by excellent aqueous solubility, increased bioavailability and are readily metabolized into the active inhibitors in vivo.

For therapeutic use, the salts of the compounds of formula (I) are those wherein the counterion is pharmaceutically or physiologically acceptable. However, salts having a pharmaceutically unacceptable counterion may also find use, for example, in the preparation or purification of a pharmaceutically acceptable compound of formula (I). All salts, whether pharmaceutically acceptable or not are included within the ambit of the present invention.

The pharmaceutically acceptable or physiologically tolerable addition salt forms which the compounds of the present invention are able to form can conveniently be prepared using the appropriate acids, such as, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methane-sulfonic, ethanesulfonic, benzenesulfonic, p-toluenesulfonic, cyclamic, salicylic, p-aminosalicylic, pamoic and the like acids.

Conversely said acid addition salt forms can be converted by treatment with an appropriate base into the free base form.

The compounds of formula (I) containing an acidic proton may also be converted into their non-toxic metal or amine addition salt form by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl, -D-glucamine, hydrabamine salts, and salts with amino acids such as, for example, arginine, lysine and the like.

Conversely said base addition salt forms can be converted by treatment with an appropriate acid into the free acid form.

The term "salts" also comprises the hydrates and the solvent addition forms which the compounds of the present invention are able to form. Examples of such forms are e.g. hydrates, alcoholates and the like.

The N-oxide forms of the present compounds are meant to comprise the compounds of formula (I) wherein one or several nitrogen atoms are oxidized to the so-called N-oxide.

The present compounds may also exist in their tautomeric forms. Such forms, although not explicitly indicated in the above formula are intended to be included within the scope of the present invention.

The term stereochemically isomeric forms of compounds of the present invention, as used hereinbefore, defines all possible compounds made up of the same atoms bonded by the same sequence of bonds but having different three-dimensional structures which are not interchangeable, which the compounds of the present invention may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods which may advantageously be employed are, for example, selective crystallization and chromatography, e.g. column chromatography.

It is clear to a person skilled in the art that the compounds of formula (I) contain at least one asymmetric center and thus may exist as different stereoisomeric forms. This asymmetric center is indicated with a asterisk (*) in the figure below.

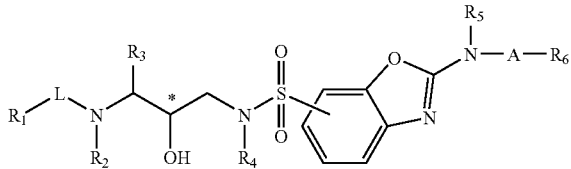

The absolute configuration of each asymmetric center that may be present in the compounds of formula (I) may be indicated by the stereochemical descriptors R and S, this R and S notation corresponding to the rules described in Pure Appl. Chem. 1976, 45, 11-30. The carbon atom marked with the asterisk (*) preferably has the R configuration.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

Whenever used hereinafter, the term "compounds of formula (I)", or "the present compounds" or similar term is meant to include the compounds of general formula (I), their N-oxides, salts, stereoisomeric forms, racemic mixtures, prodrugs, esters and metabolites, as well as their quaternized nitrogen analogues.

A suitable group of compounds are those compounds according to formula (I) wherein:

$R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, $Het^1$, $Het^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(O)$_t$, hydroxy, cyano, halogen or amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl; whereby $R_9$, $R_{10a}$ and the carbon atoms to which they are attached may also form a $C_{3-7}$cycloalkyl radical;

$R_{11a}$ is hydrogen, $C_{2-6}$alkenyl, $C_{2-6}$alkynyl, $C_{3-7}$cycloalkyl, aryl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, $Het^1$oxycarbonyl, $Het^2$oxycarbonyl, aryloxycarbonyl$C_{1-4}$alkyl, aryl$C_{1-4}$alkyloxycarbonyl, $C_{1-4}$alkylcarbonyl, $C_{3-7}$cycloalkylcarbonyl, $C_{3-7}$cycloalkyl-$C_{1-4}$alkyloxycarbonyl, $C_{3-7}$cycloalkylcarbonyloxy, carboxyl$C_{1-4}$alkylcarbonyloxy, $C_{1-4}$alkylcarbonyloxy, aryl$C_{1-4}$alkylcarbonyloxy, arylcarbonyloxy, aryloxycarbonyloxy, $Het^1$carbonyl, $Het^1$carbonyloxy, $Het^1$ $C_{1-4}$alkyloxycarbonyl, $Het^2$carbonyloxy, $Het^2C_{1-4}$alkylcarbonyloxy, $Het^2C_{1-4}$alkyloxycarbonyloxy or $C_{1-4}$alkyl optionally substituted with aryl, aryloxy, $Het^2$ or hydroxy; wherein the substituents on the amino groups are each independently selected from $C_{1-4}$alkyl, aryl, aryl$C_{1-4}$alkyl, $C_{3-7}$cycloalkyl, $C_{3-7}$cycloalkyl $C_{1-4}$alkyl, $Het^1$, $Het^2$, $Het^1C_{1-4}$alkyl and $Het^2C_{1-4}$alkyl;

$R_{11b}$ is hydrogen, $C_{3-7}$cycloalkyl, $C_{2-6}$alkenyl, $C_{2-6}$alkynyl, aryl, $Het^1$, $Het^2$ or $C_{1-4}$alkyl optionally substituted with halogen, hydroxy, $C_{1-4}$alkylS(=O)$_t$, aryl, $C_{3-7}$cycloalkyl, $Het^1$, $Het^2$, amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl;

whereby $R_{11b}$ may be linked to the remainder of the molecule via a sulfonyl group;

t is zero, 1 or 2;

L is —C(=O)—, —O—C(=O)—, —NR$_8$—C(=O)—, —O—C$_{1-6}$alkanediyl-C(=O)—, —NR$_8$—C$_{1-6}$alkanediyl-C(=O)—, —S(=O)$_2$—, —O—S(=O)$_2$—, —NR$_8$—S(=O)$_2$ whereby either the C(=O) group or the S(=O)$_2$ group is attached to the NR$_2$ moiety;

$R_4$ is hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl, or $C_{1-6}$alkyl optionally substituted with one or more substituents selected from aryl, Het$^1$, Het$^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(=O)$_p$, hydroxy, cyano, halogen and amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl-$C_{1-4}$alkyl, Het$^1$, Het$^2$, Het$^1C_{1-4}$alkyl and Het$^2C_{1-4}$alkyl; and $R_6$ is $C_{1-6}$alkyloxy, Het$^1$, Het$^1$oxy, Het$^2$, Het$^2$oxy, aryl, aryloxy or amino; and in case -A- is other than $C_{1-6}$alkanediyl then $R_6$ may also be $C_{1-6}$alkyl, Het$^1C_{1-4}$alkyl, Het$^1$oxy $C_{1-4}$alkyl, Het$^2C_{1-4}$alkyl, Het$^2$oxy$C_{1-4}$alkyl, aryl$C_{1-4}$alkyl, aryloxy$C_{1-4}$alkyl or amino$C_{1-4}$alkyl; whereby each of the amino groups in the definition of $R_6$ may optionally be substituted with one or more substituents selected from $C_{1-4}$alkyl, $C_{1-4}$alkylcarbonyl, $C_{1-4}$alkyloxycarbonyl, aryl, arylcarbonyl, aryloxycarbonyl, Het$^1$, Het$^2$, aryl$C_{1-4}$alkyl, Het$^1C_{1-4}$alkyl or Het$^2C_{1-4}$alkyl.

A particular group of compounds are those compounds of formula (I) wherein one or more of the following restrictions apply:

$R_1$ is hydrogen, Het$^1$, Het$^2$, aryl, Het$^1C_{1-6}$alkyl, Het$^2C_{1-6}$alkyl, aryl$C_{1-6}$alkyl, more in particular, $R_1$ is a saturated or partially unsaturated monocyclic or bicyclic heterocycle having 5 to 8 ring members, which contains one or more heteroatom ring members selected from nitrogen, oxygen or sulfur and which is optionally substituted, or phenyl optionally substituted with one or more substituents;

$R_2$ is hydrogen;

L is —C(=O)—, —O—C(=O)—, —O—$C_{1-6}$alkanediyl-C(=O)—, more in particular, L is —O—C(=O)— or —O—$C_{1-6}$alkanediyl-C(=O)—, whereby in each case the C(=O) group is attached to the $NR_2$ moiety;

$R_3$ is aryl$C_{1-4}$alkyl, in particular, arylmethyl, more in particular phenylmethyl;

$R_4$ is optionally substituted $C_{1-6}$alkyl, in particular unsubstituted $C_{1-6}$alkyl or $C_{1-6}$alkyl optionally substituted with one or more substituents selected from aryl, Het$^1$, Het$^2$, $C_{3-7}$cycloalkyl and amino optionally mono- or disubstituted where the substituents are selected from $C_{1-4}$alkyl, aryl, Het$^1$ and Het$^2$;

A is $C_{1-6}$alkanediyl, —C(=O)— or $C_{1-6}$alkanediyl-C(=O)—, in particular, A is 1,2-ethanediyl, 1,3-propanediyl or —C(=O)—;

$R_5$ is hydrogen, $C_{1-6}$alkyl, Het$^1C_{1-6}$alkyl, amino$C_{1-6}$alkyl whereby the amino group may optionally be mono- or di-substituted with $C_{1-4}$alkyl, in particular, $R_5$ is hydrogen or $C_{1-6}$alkyl;

$R_6$ is $C_{1-6}$alkyloxy, Het$^1$, aryl, amino; and in case -A- is other than $C_{1-6}$alkanediyl then $R_6$ may also be $C_{1-6}$alkyl, Het$^1C_{1-4}$alkyl, aryloxy$C_{1-4}$alkyl or amino$C_{1-4}$alkyl; whereby each of the amino groups may optionally be substituted; in particular, $R_6$ is $C_{1-6}$alkyloxy, optionally substituted amino; and in case -A- is other than $C_{1-6}$alkanediyl $R_6$ is $C_{1-6}$alkyl;

-A-$R_6$ is hydroxy$C_{1-6}$alkyl; or $R_5$ and -A-$R_6$ taken together with the nitrogen atom to which they are attached may also form Het$^1$.

A special group of compounds are those compounds of formula (I) wherein $R_1$ is Het$^1$, aryl, Het$^2C_{1-6}$alkyl; $R_2$ is hydrogen; L is —C(=O)—, —O—C(=O)—, —O—CH$_2$—C(=O)—, whereby in each case the C(=O) group is attached to the $NR_2$ moiety; $R_3$ is phenyl-methyl; and $R_4$ is $C_{1-6}$alkyl.

Also a special group of compounds are those compounds of formula (I) wherein A is $C_{1-6}$alkanediyl or —C(=O)—; $R_5$ is hydrogen or methyl; $R_6$ is $C_{1-6}$alkyloxy, Het$^1$, amino; and in case -A- is other than $C_{1-6}$alkanediyl then $R_6$ may also be $C_{1-6}$alkyl, Het$^1C_{1-4}$alkyl or amino$C_{1-4}$alkyl; whereby each of the amino groups may optionally be substituted.

A suitable group of compounds are those compounds of formula (I) wherein A is $C_{1-6}$alkanediyl or —C(=O)—; $R_5$ is hydrogen or methyl; $R_6$ is Het$^2$; and in case -A- is other than $C_{1-6}$alkanediyl then $R_6$ may also be Het$^2C_{1-4}$alkyl; whereby each of the amino groups may be optionally substituted.

Yet another special group of compounds are those compounds of formula (I) wherein A is —C(=O)— and $R_6$ is $C_{1-6}$alkyloxy or $C_{1-6}$alkyl.

Another group of compounds are those compounds of formula (I) wherein wherein A is —C(=O)— and $R_6$ is Het$^2$, Het$^1$ or optionally mono- or disubstituted amino$C_{1-6}$alkyl.

An interesting group of compounds are those compounds of formula (I) wherein -A- is carbonyl and $R_6$ is aryl, Het$^1C_{1-4}$alkyl, aryloxy$C_{1-4}$alkyl or amino$C_{1-4}$alkyl, whereby the amino groups may optionally be substituted; or -A- is carbonyl, $R_6$ is $C_{1-4}$alkyl and $R_5$ is Het$^1C_{1-6}$alkyl or amino$C_{1-6}$alkyl whereby the amino group may optionally be mono- or di-substituted with $C_{1-4}$alkyl .

Another interesting group of compounds are those compounds of formula (I) wherein -A- is $C_{1-6}$alkanediyl and $R_6$ is amino and Het$^1$; whereby the amino group may optionally be mono- or di-substituted with $C_{1-4}$alkyl.

Another interesting group of compounds are those compounds of formula (I) wherein $R_1$ hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, Het$^1$, Het$^1C_{1-6}$alkyl, Het$^2$, Het$^2C_{1-6}$alkyl; wherein Het$^1$ in the definition of $R_1$ is a saturated or partially unsaturated monocyclic heterocycle having 5 or 6 ring members, which contains one or more heteroatom ring members selected from nitrogen, oxygen or sulfur and which is optionally substituted on one or more carbon atoms.

Another interesting group of compounds are those compounds of formula (I) wherein L is —O—$C_{1-6}$alkanediyl-C(=O)—.

Another interesting group of compounds are those compounds of formula (I) wherein A is $C_{1-6}$alkanediyl, —C(=O)— or $C_{1-6}$alkanediyl-C(=O)—; whereby the point of attachment to the nitrogen atom is the $C_{1-6}$alkanediyl group in those moieties containing said group;

$R_5$ is hydrogen, $C_{1-6}$alkyl, Het$^1C_{1-6}$alkyl, Het$^2C_{1-6}$alkyl, amino$C_{1-6}$alkyl whereby the amino group may optionally be mono- or di-substituted with $C_{1-4}$alkyl; and in case -A- is —C(=O)— then $R_6$ is $C_{1-6}$alkyloxy, Het$^1$, Het$^1$oxy or Het$^2$oxy, aryl, Het$^1C_{1-4}$alkyl, Het$^1$oxy $C_{1-4}$alkyl, Het$^2C_{1-4}$alkyl, Het$^2$oxy$C_{1-4}$alkyl, aryl$C_{1-4}$alkyl, aryloxy$C_{1-4}$alkyl or amino$C_{1-4}$alkyl; and in case -A- is $C_{1-6}$alkanediyl then $R_6$ is amino, $C_{1-6}$alkyloxy, Het$^1$, Het$^1$oxy or Het oxy; and in case -A- is $C_{1-6}$alkanediyl-C(=O)— then $R_6$ is $C_{1-6}$alkyloxy, Het$^1$, Het$^1$oxy or Het$^2$oxy, aryl, $C_{1-6}$alkyl, Het$^1C_{1-4}$alkyl, Het$^1$oxy$C_{1-4}$alkyl, Het$^2C_{1-4}$alkyl, Het$^2$oxy$C_{1-4}$alkyl, aryl$C_{1-4}$alkyl, aryloxy$C_{1-4}$alkyl or amino$C_{1-4}$alkyl;

whereby each of the amino groups in the definition of $R_6$ may optionally be substituted with one or more substituents selected from $C_{1-4}$alkyl, $C_{1-4}$alkylcarbonyl, $C_{1-4}$alkyloxycarbonyl, aryl, arylcarbonyl, aryloxycarbonyl, Het$^1$, Het$^2$, aryl-$C_{1-4}$alkyl, Het$^1C_{1-4}$alkyl or Het$^2C_{1-4}$alkyl; and $R_5$ and -A-$R_6$ taken together with the nitrogen atom to which they are attached may also form $Het^1$ whereby $Het^1$ is substituted by at least an oxo group.

A particular group of compounds are those compounds of formula (I) wherein one or more of the following restrictions apply:

$R_1$ is hydrogen, $Het^1$, $Het^2$, aryl, $Het^1C_{1-6}$alkyl, $Het^2C_{1-6}$alkyl, aryl$C_{1-6}$alkyl, more in particular, $R_1$ is a saturated or partially unsaturated monocyclic or bicyclic heterocycle having 5 to 8 ring members, which contains one or more heteroatom ring members each independently selected from nitrogen, oxygen or sulfur and which is optionally substituted, or phenyl optionally substituted with one or more substituents;

$R_2$ is hydrogen;

L is —C(=O)—, —O—C(=O)—, —O—$C_{1-6}$alkanediyl-C(=O)—, more in particular, L is —O—C(=O)— or —O—$C_{1-6}$alkanediyl-C(=O)—, whereby in each case the C(=O) group is attached to the $NR_2$ moiety;

$R_3$ is aryl$C_{1-4}$alkyl, in particular, arylmethyl, more in particular phenylmethyl;

$R_4$ is optionally substituted $C_{1-6}$alkyl, in particular unsubstituted $C_{1-6}$alkyl or $C_{1-6}$alkyl optionally substituted with one or more substituents each independently selected from aryl, $Het^1$, $Het^2$, $C_{3-7}$cycloalkyl and amino optionally mono- or disubstituted where the substituents are each independently selected from $C_{1-4}$alkyl, aryl, $Het^1$ and $Het^2$;

A is $C_{1-6}$alkanediyl, —C(=O)— or $C_{1-6}$alkanediyl-C(=O)—, in particular, A is 1,2-ethanediyl, 1,3-propanediyl or —C(=O)—;

$R_5$ is hydrogen, $C_{1-6}$alkyl, $Het^1C_{1-6}$alkyl, amino$C_{1-6}$alkyl whereby the amino group may optionally be mono- or di-substituted with $C_{1-4}$alkyl, in particular, $R_5$ is hydrogen or $C_{1-6}$alkyl;

$R_6$ is $C_{1-6}$alkyloxy, $Het^1$, aryl, amino; and in case -A- is other than $C_{1-6}$alkanediyl then $R_6$ may also be $C_{1-6}$alkyl, $Het^1C_{1-4}$alkyl, aryloxy$C_{1-4}$alkyl or amino$C_{1-6}$alkyl; whereby each of the amino groups may optionally be substituted; in particular, $R_6$ is $C_{1-6}$alkyloxy, optionally substituted amino; and in case -A- is other than $C_{1-6}$alkanediyl $R_6$ is $C_{1-6}$alkyl;

-A-$R_6$ is hydroxy$C_{1-6}$alkyl; or $R_5$ and -A-$R_6$ taken together with the nitrogen atom to which they are attached may also form $Het^1$.

Another interesting group of compounds are those compounds of formula (I) wherein -A- is $C_{1-6}$alkanediyl and $R_6$ is amino or $Het^1$; whereby the amino group may optionally be mono- or di-substituted with $C_{1-4}$alkyl.

Another interesting group of compounds are those compounds of formula (I) wherein A is $C_{1-6}$alkanediyl, —C(=O)— or $C_{1-6}$alkanediyl-C(=O)—; whereby the point of attachment to the nitrogen atom is the $C_{1-6}$alkanediyl group in those moieties containing said group;

$R_5$ is hydrogen, $C_{1-6}$alkyl, $Het^1C_{1-6}$alkyl, $Het^2C_{1-6}$alkyl, amino$C_{1-6}$alkyl whereby the amino group may optionally be mono- or di-substituted with $C_{1-4}$alkyl; and in case -A- is —C(=O)— then $R_6$ is $C_{1-6}$alkyloxy, $Het^1$, $Het^1$oxy or $Het^2$oxy, aryl, $Het^1C_{1-4}$alkyl, $Het^1$oxy$C_{1-4}$alkyl, $Het^2C_{1-4}$alkyl, $Het^2$oxy$C_{1-4}$alkyl, aryl$C_{1-4}$alkyl, aryloxy$C_{1-4}$alkyl or amino$C_{1-4}$alkyl; and in case -A- is $C_{1-6}$alkanediyl then $R_6$ is amino, $C_{1-6}$alkyloxy, $Het^1$, $Het^1$oxy or $Het^2$oxy; and in case -A- is $C_{1-6}$alkanediyl-C(=O)— then $R_6$ is $C_{1-6}$alkyloxy, $Het^1$, $Het^1$oxy or $Het^2$oxy, aryl, $C_{1-4}$alkyl, $Het^1C_{1-4}$alkyl, $Het^1$oxy$C_{1-4}$alkyl, $Het^2C_{1-4}$alkyl, $Het^2$oxy$C_{1-4}$alkyl, aryl$C_{1-4}$alkyl, aryloxy$C_{1-4}$alkyl or amino$C_{1-4}$alkyl;

whereby each of the amino groups in the definition of $R_6$ may optionally be substituted with one or more substituents each independently selected from $C_{1-4}$alkyl, $C_{1-4}$alkylcarbonyl, $C_{1-4}$alkyloxycarbonyl, aryl, arylcarbonyl, aryloxycarbonyl, $Het^1$, $Het^2$aryl$C_{1-4}$alkyl, $Het^1C_{1-4}$alkyl or $Het^2C_{1-4}$alkyl; and $R_5$ and -A-$R_6$ taken together with the nitrogen atom to which they are attached may also form $Het^1$ whereby $Het^1$ is substituted by at least an oxo group.

Another group of compounds are those of formula (I) wherein $R_1$ is $Het^2C_{1-6}$alkyl, L is —C(=O)—, —O—C(=O)—, —O—$C_{1-6}$alkanediyl-C(=O)—; in particular the $Het^2$ moiety in the definition of $R_1$ is an aromatic heterocycle having 5 or 6 ring members, which contain one or more heteroatom ring members each independently selected from nitrogen, oxygen or sulfur, more in particular the $Het^2$ moiety is an aromatic heterocycle having 5 or 6 ring members, which contain two or more heteroatom ring members each independently selected from nitrogen, oxygen or sulfur.

Suitably, the $SO_2$ moiety of the sulfonamide in the compounds of the present invention is para vis-à-vis the nitrogen of the benzoxazole moiety.

Another group of suitable compounds are those of formula (I) wherein A is $C_{1-6}$alkane-diyl or —C(=O)—; $R_5$ is hydrogen or methyl; and $R_6$ is $C_{1-6}$alkyloxy, $Het^1$, $Het^2$, amino or amino $C_{1-6}$alkyl; whereby each amino optionally may be mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl.

Another group of suitable compounds are those of formula (I) wherein $R_1$ is $Het^2$ or $Het^2C_{1-6}$alkyl; wherein said $Het^2$ in the definition of $R_1$ is an aromatic heterocycle having at least one heteroatom each independently selected from nitrogen, oxygen and sulfur; L is —C(=O)—, —O—C(=O)— or —O—$C_{1-6}$alkyl-C(=O)—; A is $C_{1-6}$alkanediyl or —C(=O)—; $R_5$ is hydrogen or methyl; and $R_6$ is $C_{1-6}$alkyloxy, $Het^1$, $Het^2$, amino or amino$C_{1-6}$alkyl; whereby each amino optionally may be mono- or disubstituted, where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl.

Another group of suitable compounds are those of formula (I) wherein $R_1$ is 2-thiazolylmethyl-; and L is —O—C(=O)—.

Another group of suitable compounds are those of formula (I) wherein $R_5$ is hydrogen; A is —C(=O)—; and $R_6$ is $Het^2$; wherein said $Het^2$ contains 5 or 6 ring members and one heteroatom selected from nitrogen, oxygen or sulfur.

Another group of compounds are those of formula (I) wherein $R_1$ is $Het^1$, having 8 ring members and two heteroatoms each independently selected from nitrogen, oxygen or sulfur; L is —O—C(=O)—; $R_5$ is hydrogen or methyl; A is —C(=O)—, $C_{1-6}$alkanediyl; and $R_6$ is optionally mono- or disubstituted amino$C_{1-4}$alkyl, $Het^1$ or $Het^2$; wherein said $Het^2$ contains 5 or 6 ring members and one heteroatom selected from nitrogen, oxygen or sulfur; wherein the amino substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl.

The compounds of formula (I) can generally be prepared using procedures analogous to those procedures described in WO 95/06030, WO 96/22287, WO 96/28418, WO 96/28463, WO 96/28464, WO 96/28465 and WO 97/18205.

Particular reaction procedures to make the present compounds are described below. In the preparations described below, the reaction products may be isolated from the medium and, if necessary, further purified according to methodologies generally known in the art such as, for example, extraction, crystallization, trituration and chromatography.

The 2-acetamido-6-chlorosulfonylbenzoxazole (intermediate a-2) was prepared following the procedure described in EP-A-0,445,926.

Intermediates a-4 were prepared by reacting an intermediate a-3, prepared according to the procedure described in WO97/1 8205 and also depicted in scheme C, with an intermediate a-2 in a reaction-inert solvent such as dichloromethane, and in the presence of a base such as triethylamine and at low temperature, for example at 0° C. The Boc group in the intermediate a-3 is a protective tert-butyloxycarbonyl

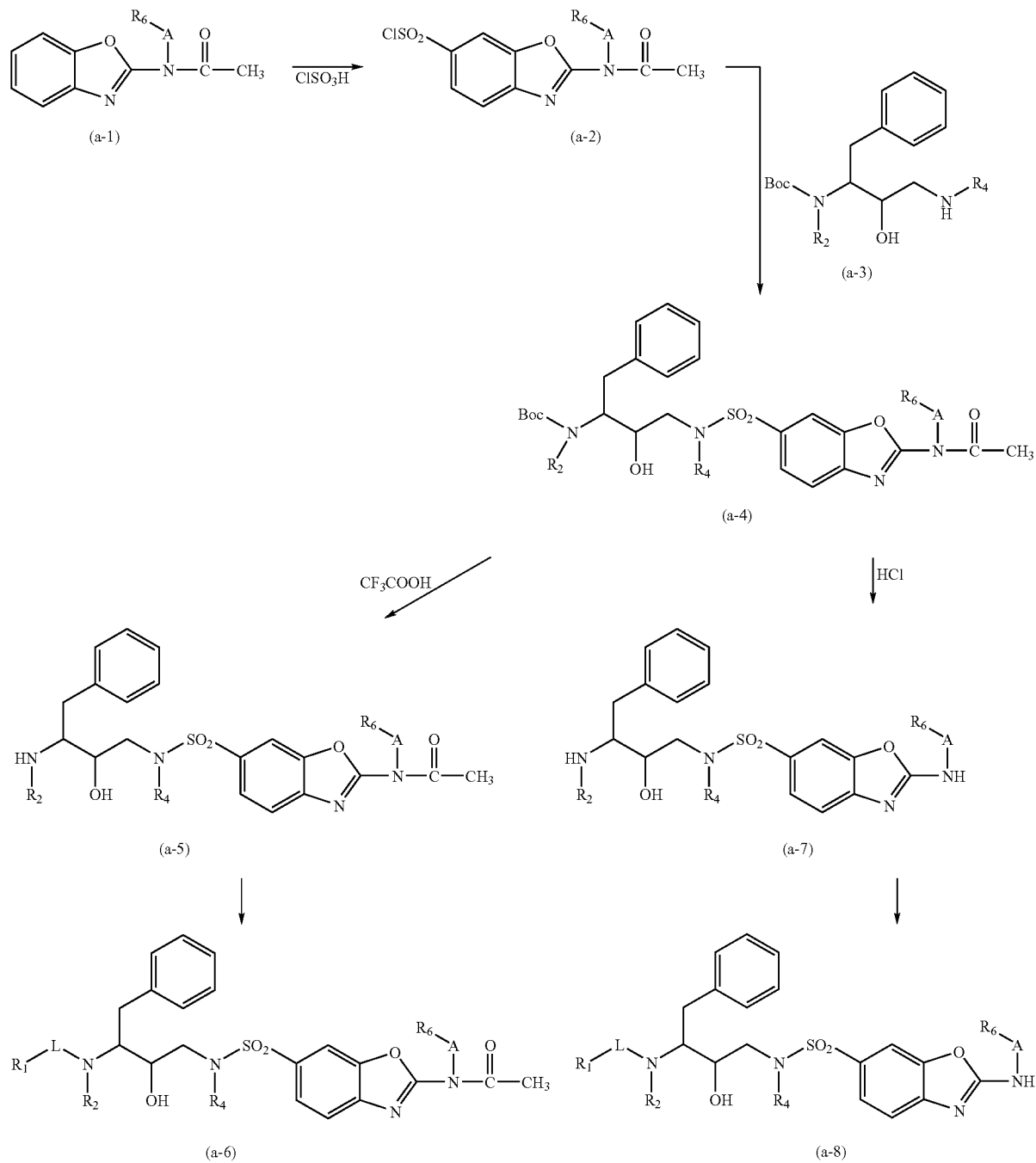

group. It may conveniently be replaced by another suitable protective group such as phtalimido or benzyloxycarbonyl. Using intermediate a-4 as a starting material, intermediate a-5 was deprotected using an acid such as trifluoroacetic acid in a suitable solvent such as dichloromethane. The resulting intermediate may be further reacted with an intermediate of formula $R_1$-L-(leaving group) in the presence of a base such as triethylamine and optionally in the presence of 1-(3-dimethylaminopropyl)-3-ethylcarbodiimide hydrochloric acid (EDC) or an alcohol such as tert-butanol, and in a suitable solvent such as dichloromethane; thus forming intermediates a-6. Particularly, intermediates of formula $R_1$—C(=O)—OH are suitable to further react with an intermediate a-5.

Alternatively, intermediates a-4 may be deprotected with a strong acid such as hydrochloric acid in isopropanol, in a suitable solvent such as a mixture of ethanol and dioxane, thus preparing an intermediate a-7. Intermediates a-8 can be prepared analogously to the procedure described for the preparation of intermediates a-6.

The procedure described in scheme A may also be used to prepare intermediates of formula a-6 wherein benzoxazole is substituted with a carbamate instead of an amide.

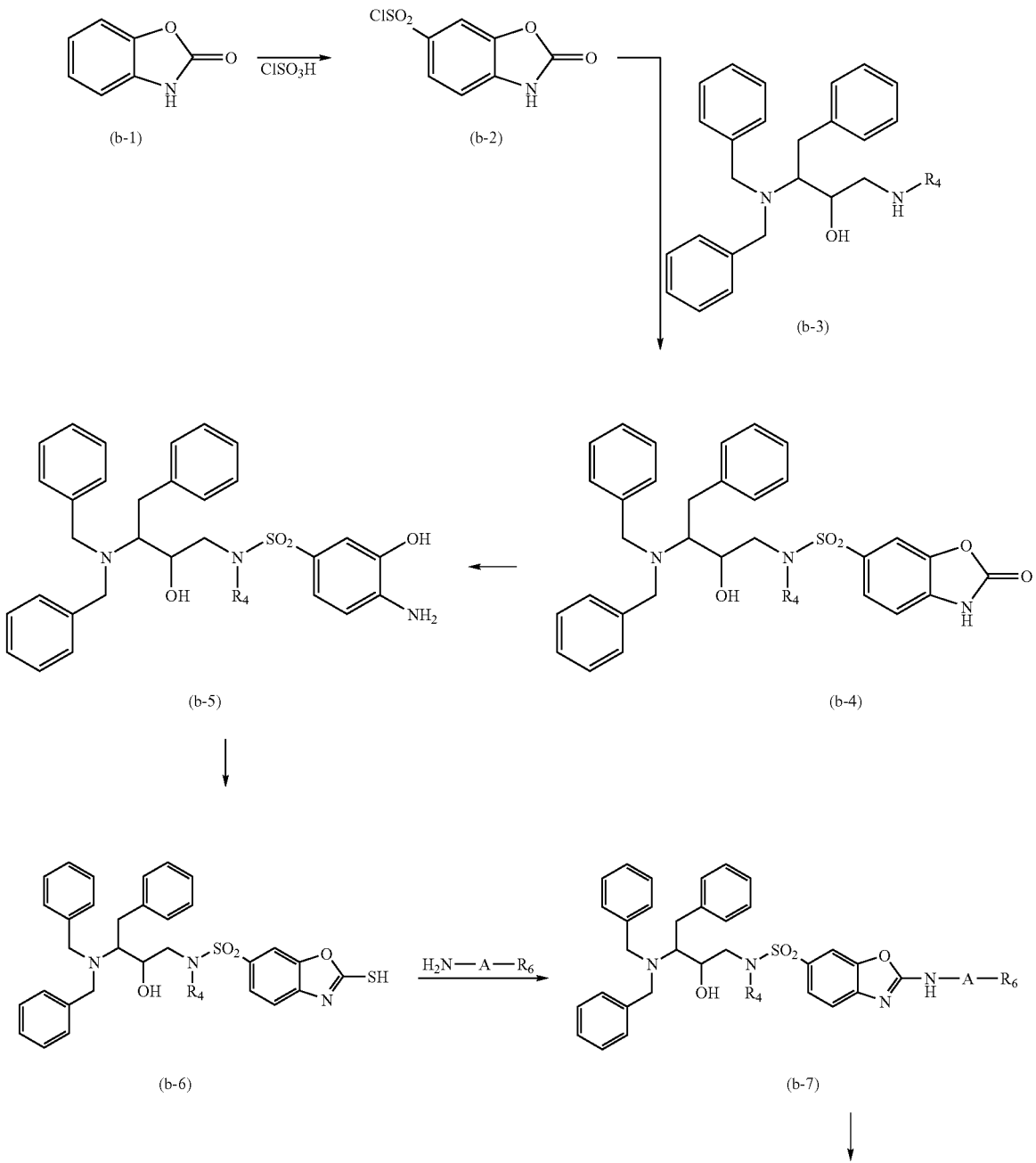

-continued

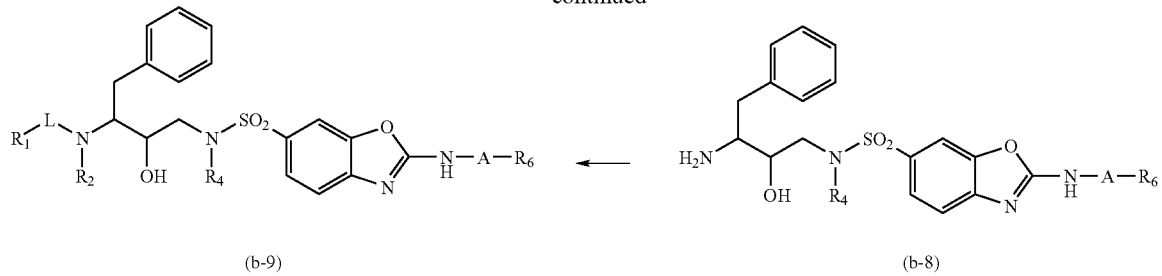

(b-9)　　　　　　　　　　　　　　　　(b-8)

Intermediate b-4 can be prepared according to the procedure described in scheme A. Intermediate b-5 can be prepared by for instance refluxing the 2(3H)-benzoxazolone derivative b-4 in the presence of a base such as, for example, sodium-hydroxide. Said intermediate b-5 can then be cyclized again using a reagent such as alkyl xanthic acid potassium salt (alkyl dithiocarbonate potassium salt) in a suitable solvent such as, for example, ethanol at reflux temperature, thus preparing a 2(3H)-benzoxazolethione of formula b-6. Intermediate b-6 may then be derivatized with an amine of formula $H_2N$-A-$R_6$ in a suitable solvent such as acetonitrile to obtain an intermediate b-7.

Debenzylation may be performed using art-known techniques such as the use of Pd on carbon in the presence of $H_2$ in a suitable solvent. The thus formed intermediate of formula b-8 may then be reacted with an intermediate of formula $R_1$-L-(leaving group) in the presence of a base such as triethylamine and optionally in the presence of EDC or an alcohol such as tert-butanol, and in a suitable solvent such as dichloromethane, thus obtaining an intermediate b-9.

A particular way of preparing acetamide substituted benzoxazoles is depicted in scheme C.

Scheme C

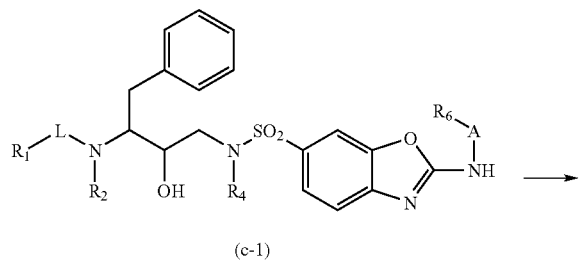

(c-1)

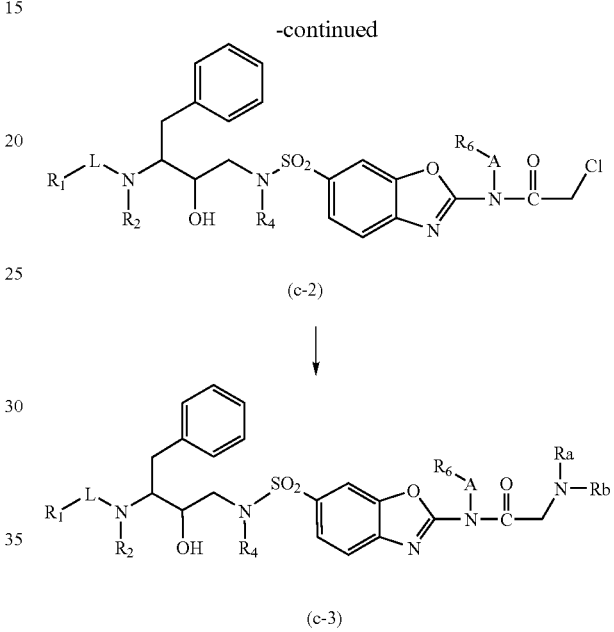

(c-2)

(c-3)

Intermediate c-1, prepared following the procedure as described in Scheme A, may be reacted with chloroacetylchloride, or a functional analogue, in the presence of a base such as triethylamine and in a solvent such as 1,4-dioxane in order to obtain an amide of formula c-2. Said intermediate c-2 can further be reacted with an amine of formula $NR_aR_b$ whereby $R_a$ and $R_b$ are defined as the possible substituents on an amino group in the variable $R_6$.

Another particular way of preparing acetamide substituted benzoxazoles is depicted in scheme D.

Scheme D

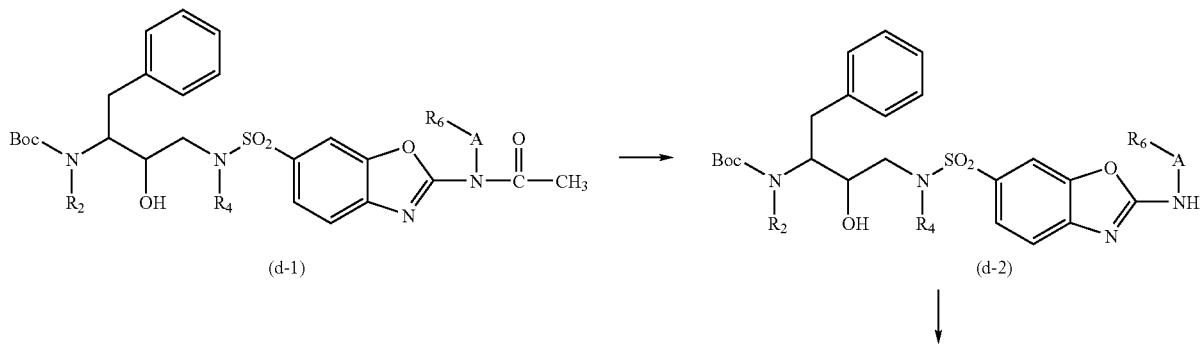

(d-1)　　　　　　　　　　　　　　　　(d-2)

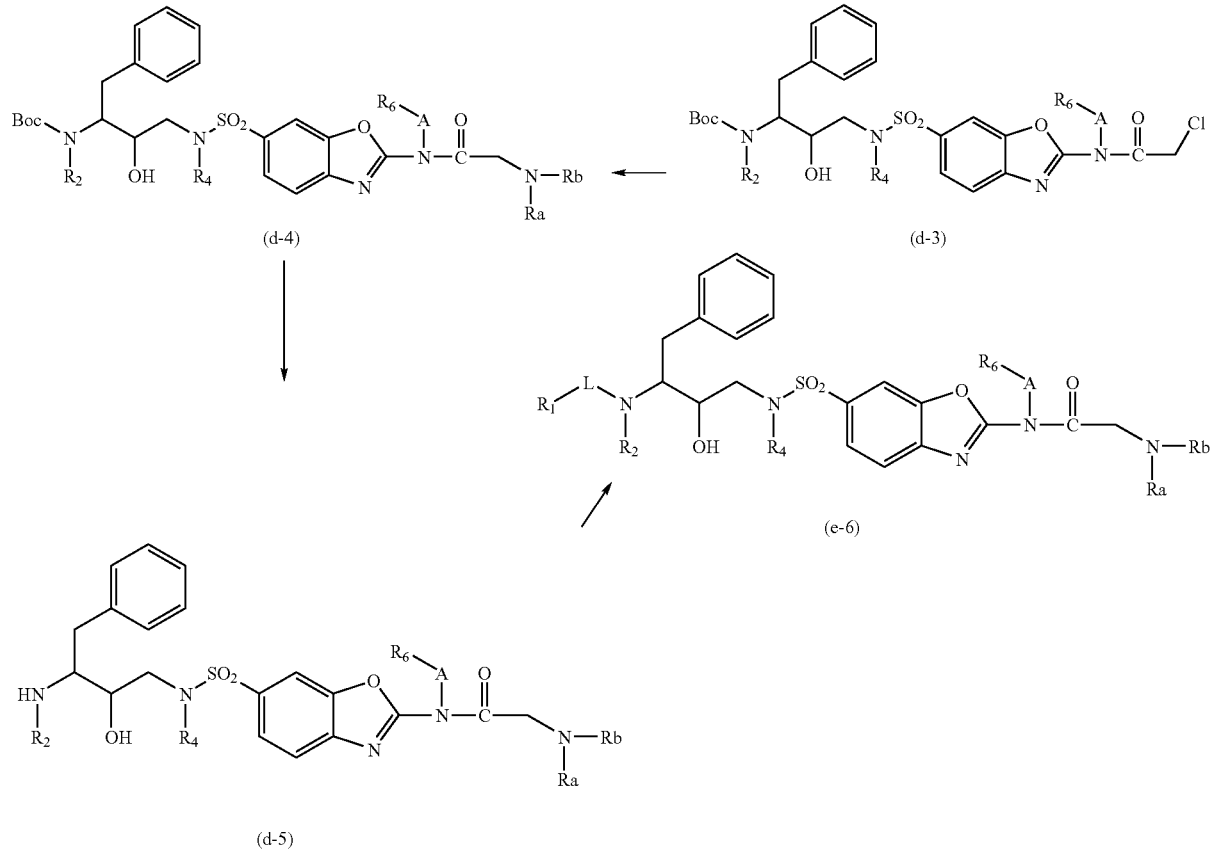

(d-4) (d-3)

(e-6)

(d-5)

Intermediate d-2 can be prepared by treating intermediate d-1, prepared following the procedure described in scheme A, with a base such as sodiumcarbonate in an aqueous medium such as a water dioxane mixture. The synthesis steps depicted in scheme D to obtain intermediate d-6 are all analogous to reaction procedures described in the above synthesis schemes.

A number of intermediates and starting materials used in the foregoing preparations are known compounds, while others may be prepared according to art-known methodologies of preparing said or similar compounds.

Scheme E

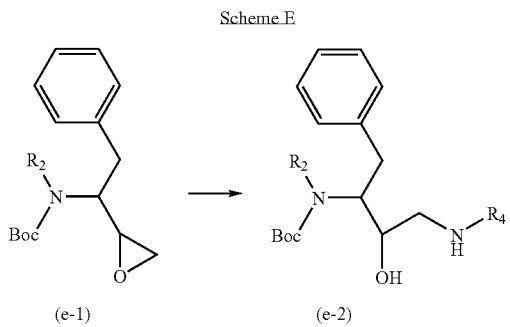

(e-1) (e-2)

Intermediate e-2, corresponding to intermediate a-3 in scheme A, may be prepared by adding an amine of formula $H_2N-R_4$ to an intermediate e-1 in a suitable solvent such as isopropanol.

Scheme F

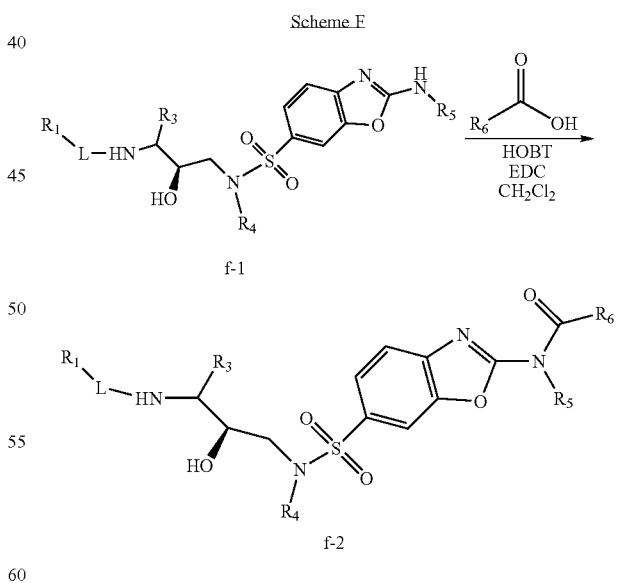

f-1 f-2

A mixture of the 2-aminobenzoxazole f-1 in dichloromethane was stirred under an inert atmosphere such as nitrogen. $R_6$—COOH, EDC and HOBT (1-hydroxy-1-H-benzotriazole) were added. The mixture was stirred at room temperature for 48 h. Water was added, the water layer was extracted with dichloromethane and the combined organic layers were washed with brine, dried under MgSO$_4$ and the solvent was evaporated under reduced pressure. Purification was performed on silica yielding f-2.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

An interesting group of intermediates are those intermediates of formula a-8, b-8 or c-1 wherein -A-R$_6$ is hydrogen. Said intermediates may also have pharmacological properties similar to those pharmacological properties of the compounds of formula (I).

The present compounds can thus be used in animals, preferably in mammals, and in particular in humans as pharmaceuticals per se, in mixtures with one another or in the form of pharmaceutical preparations.

Furthermore, the present invention relates to pharmaceutical preparations which as active constituents contain an effective dose of at least one of the compounds of formula (I) in addition to customary pharmaceutically innocuous excipients and auxiliaries. The pharmaceutical preparations normally contain 0.1 to 90% by weight of a compound of formula (I). The pharmaceutical preparations can be prepared in a manner known per se to one of skill in the art. For this purpose, at least one of a compound of formula (I), together with one or more solid or liquid pharmaceutical excipients and/or auxiliaries and, if desired, in combination with other pharmaceutical active compounds, are brought into a suitable administration form or dosage form which can then be used as a pharmaceutical in human medicine or veterinary medicine.

Pharmaceuticals which contain a compound according to the invention can be administered orally, parenterally, e.g., intravenously, rectally, by inhalation, or topically, the preferred administration being dependent on the individual case, e.g., the particular course of the disorder to be treated. Oral administration is preferred.

The person skilled in the art is familiar on the basis of his expert knowledge with the auxiliaries which are suitable for the desired pharmaceutical formulation. Beside solvents, gel-forming agents, suppository bases, tablet auxiliaries and other active compound carriers, antioxidants, dispersants, emulsifiers, antifoams, flavor corrigents, preservatives, solubilizers, agents for achieving a depot effect, buffer substances or colorants are also useful.

Due to their favorable pharmacological properties, particularly their activity against multi-drug resistant HIV protease enzymes, the compounds of the present invention are useful in the treatment of individuals infected by HIV and for the prophylaxis of these individuals. In general, the compounds of the present invention may be useful in the treatment of warm-blooded animals infected with viruses whose existence is mediated by, or depends upon, the protease enzyme. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1. Consequently, the compounds of the present invention can be used in the manufacture of a medicament useful for treating conditions associated with HIV and other pathogenic retroviruses, in particular medicaments useful for treating patients infected with multi-drug resistant HIV virus.

In a preferred embodiment, the invention relates to the use of a compound of formula (I) or any subgroup thereof in the manufacture of a medicament for treating or combating infection or disease associated with multi-drug resistant retrovirus infection in a mammal, in particular HIV-1 infection. Thus, the invention also relates to a method of treating a retroviral infection, or a disease associated with multi-drug resistant retrovirus infection comprising administering to a mammal in need thereof an effective amount of a compound of formula (I) or a subgroup thereof.

In another preferred embodiment, the present invention relates to the use of formula (I) or any subgroup thereof in the manufacture of a medicament for inhibiting a protease of a multi-drug resistant retrovirus in a mammal infected with said retrovirus, in particular HIV-1 retrovirus.

In another preferred embodiment, the present invention relates to the use of formula (I) or any subgroup thereof in the manufacture of a medicament for inhibiting multi-drug resistant retroviral replication, in particular HIV-1 replication.

The compounds of the present invention may also find use in inhibiting ex vivo samples containing HIV or expected to be exposed to HIV. Hence, the present compounds may be used to inhibit HIV present in a body fluid sample which contains or is suspected to contain or be exposed to HIV.

Also, the combination of an antiretroviral compound and a compound of the present invention can be used as a medicine. Thus, the present invention also relates to a product containing (a) a compound of the present invention, and (b) another antiretroviral compound, as a combined preparation for simultaneous, separate or sequential use in treatment of retroviral infections, in particular, in the treatment of infections with multi-drug resistant retroviruses. Thus, to combat or treat HIV infections, or the infection and disease associated with HIV infections, such as Acquired Immunodeficiency Syndrome (AIDS) or AIDS Related Complex (ARC), the compounds of this invention may be co-administered in combination with for instance, binding inhibitors, such as, for example, dextran sulfate, suramine, polyanions, soluble CD4; fusion inhibitors, such as, for example, T20, T1249, SHC-C; co-receptor binding inhibitors, such as, for example, AMD 3100 (Bicyclams), TAK 779; RT inhibitors, such as, for example, foscarnet and prodrugs; nucleoside RTIs, such as, for example, AZT, 3TC, DDC, DDI, D4T, Abacavir, FTC, DAPD, dOTC; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, TMC-120, MKC-442, UC 781, UC 782, Capravirine, DPC 961, DPC963, DPC082, DPC083, calanolide A, SJ-3366, TSAO, 4"-deaminated TSAO; RNAse H inhibitors, such as, for example, SP1093V, PD126338; TAT inhibitors, such as, for example, RO-5-3335, K12, K37; integrase inhibitors, such as, for example, L 708906, L 731988; protease inhibitors, such as, for example, amprenavir, ritonavir, nelfinavir, saquinavir, indinavir, lopinavir, palinavir, BMS 186316, BMS 232632, DPC 681, DPC 684, tipranavir, AG1776, DMP 450, GS3333, KNI-413, KNI-272, L754394, L756425, LG-71350, PD161374, PD173606, PD177298, PD178390, PD178392, PNU 140135, maslinic acid, U-140690; glycosylation inhibitors, such as, for example, castanospermine, deoxynojirimycine.

The combination may in some cases provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, and naltrexone) with antibiotics (e.g., pentamidine isothiorate) cytokines (e.g. Th2), modulators of cytokines, chemokines (e.g. $CCR_5$) or hormones (e.g. growth hormone) to ameliorate, combat, or eliminate HIV infection and its symptoms.

The compounds of the present invention may also be administered in combination with modulators of the metabolization following application of the drug to an individual. These modulators include compounds that interfere with the metabolization at cytochromes, such as cytochrome P450. It is known that several isoenzymes exist of cytochrome P450, one of which is cytochrome P450 3A4. Ritonavir is an example of a modulator of metabolization via cytochrome P450.

For an oral administration form, compounds of the present invention are mixed with suitable additives, such as excipients, stabilizers or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms.

For subcutaneous or intravenous administration, the active compounds, if desired with the substances customary therefor such as solubilizers, emulsifiers or further auxiliaries, are brought into solution, suspension, or emulsion. The compounds of formula (I) can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned.

Suitable pharmaceutical formulations for administration in the form of aerosols or sprays are, for example, solutions, suspensions or emulsions of the compounds of formula (I) or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant. Such a preparation customarily contains the active compound in a concentration from approximately 0.1 to 50%, in particular from approximately 0.3 to 3% by weight.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

Appropriate cyclodextrins are α-, β- or γ-cyclodextrins (CDs) or ethers and mixed ethers thereof wherein one or more of the hydroxy groups of the anhydroglucose units of the cyclodextrin are substituted with $C_{1-6}$alkyl, particularly methyl, ethyl or isopropyl, e.g. randomly methylated β-CD; hydroxy$C_{1-6}$alkyl, particularly hydroxyethyl, hydroxypropyl or hydroxybutyl; carboxy$C_{1-6}$alkyl, particularly carboxymethyl or carboxyethyl; $C_{1-6}$alkyl-carbonyl, particularly acetyl; $C_{1-6}$alkyloxycarbonyl$C_{1-6}$alkyl or carboxy$C_{1-6}$alkyloxy$C_{1-6}$alkyl, particularly carboxymethoxypropyl or carboxyethoxypropyl; $C_{1-6}$alkylcarbonyloxy$C_{1-6}$alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, 2-hydroxy-propyl-γ-CD and (2-carboxymethoxy)propyl-β-CD, and in particular 2-hydroxypropyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

An interesting way of formulating the present compounds in combination with a cyclodextrin or a derivative thereof has been described in EP-A-721,331. Although the formulations described therein are with antifungal active ingredients, they are equally interesting for formulating the compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. Said formulations may also be rendered more palatable by adding pharmaceutically acceptable sweeteners and/or flavors.

Other convenient ways to enhance the solubility of the compounds of the present invention in pharmaceutical compositions are described in WO 94/05263, WO 98/42318, EP-A-499,299 and WO 97/44014, all incorporated herein by reference.

More in particular, the present compounds may be formulated in a pharmaceutical composition comprising a therapeutically effective amount of particles consisting of a solid dispersion comprising (a) a compound of formula (I), and (b) one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermo-dynamics, such a solid dispersion is referred to as "a solid solution". Solid solutions are preferred physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa·s when dissolved in a 2% aqueous solution at 20° C. solution.

Preferred water-soluble polymers are hydroxypropyl methylcelluloses or HPMC. HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxy-propyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Various techniques exist for preparing solid dispersions including melt-extrusion, spray-drying and solution-evaporation, melt-extrusion being preferred.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the present compounds involves a pharmaceutical composition whereby the present compounds are incorporated in hydrophilic polymers and applying this mixture as a coat film over many small beads, thus yielding a composition with good bioavailability which can conveniently be manufactured and which is suitable for preparing pharmaceutical dosage forms for oral administration.

Said beads comprise (a) a central, rounded or spherical core, (b) a coating film of a hydrophilic polymer and an antiretroviral agent and (c) a seal-coating polymer layer.

Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

Another aspect of the present invention concerns a kit or container comprising a compound of formula (I) in an amount effective for use as a standard or reagent in a test or assay for determining the ability of a potential pharmaceutical to inhibit HIV protease, HIV growth, or both. This aspect of the invention may find its use in pharmaceutical research programs.

The compounds of the present invention can be used in phenotypic resistance monitoring assays, such as known recombinant assays, in the clinical management of resistance developing diseases such as HIV. A particularly useful resistance monitoring system is a recombinant assay known as the Antivirogram™. The Antivirogram™ is a highly automated, high throughput, second generation, recombinant assay that can measure susceptibility, especially viral susceptibility, to the compounds of the present invention. (Hertogs K, de Bethune M P, Miller V et al. *Antimicrob Agents Chemother,* 1998; 42(2):269-276, incorporated by reference).

The compounds of the present invention may also be linked to maleimide or derivatives thereof to form conjugates.

The dose of the present compounds or of the physiologically tolerable salt(s) thereof to be administered depends on the individual case and, as customary, is to be adapted to the conditions of the individual case for an optimum effect. Thus it depends, of course, on the frequency of administration and on the potency and duration of action of the compounds employed in each case for therapy or prophylaxis, but also on the nature and severity of the infection and symptoms, and on the sex, age, weight and individual responsiveness of the human or animal to be treated and on whether the therapy is acute or prophylactic. Customarily, the daily dose of a compound of formula (I) in the case of administration to a patient approximately 75 kg in weight is 1 mg to 3 g, suitably 1 mg to 1 g, preferably 3 mg to 0.5 g, more preferably 5 mg to 300 mg. The dose can be administered in the form of an individual dose, or divided into several, e.g. two, three, or four, individual doses.

Experimental Part

Preparation of the Compounds of Formula (I) and Their Intermediates

EXAMPLE 1

Preparation of Compound 1 a) A mixture of 5 g 2-acetamidobenzoxazole and 20 ml chlorosulfonic acid in dichloromethane was heated to 60° C. for 2 hours (h). After cooling the mixture was poured into ice. The organic layer was separated and dried over $MgSO_4$, thus yielding 2-acetamido-6-chlorosulfonylbenzoxazole (interm. 1)

b) A mixture of 3.4 g of [(1S,2R)-2-hydroxy-3-[(2-methylpropyl)amino]-1-(phenylmethyl)propyl]carbamic acid 1,1-dimethylethyl ester, prepared analogously to the procedure described in WO 97/18205, and 2.6 g of triethylamine in 100 ml of dichloromethane was stirred at 0° C. Then 2.8 g of 2-acetamido-6-chlorosulfonylbenzoxazole was added and the reaction mixture stirred overnight at room temperature. After washing with water, the organic layer was separated, dried and evaporated. The brown solid obtained was reslurried in warm diisopropyl ether, cooled and filtered off, thus yielding 88% (5.1 g) of interm. 2:

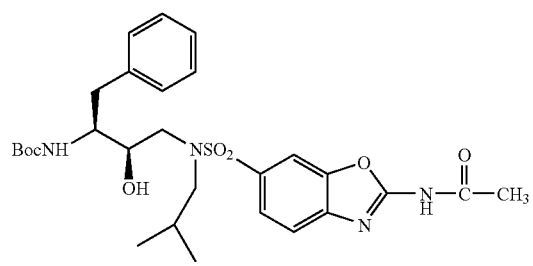

c) To a mixture of 1.2 g of intermediate 2 in 25 ml of dichloromethane, 2.3 ml of trifluoracetic acid were added. The reaction mixture as stirred at room temperature for 6 hours. Extra dichloromethane was added and washed with NaHCO$_3$ solution. The organic layer was dried and evaporated under reduced pressure, yielding 970 mg (99%) of intermediate 3:

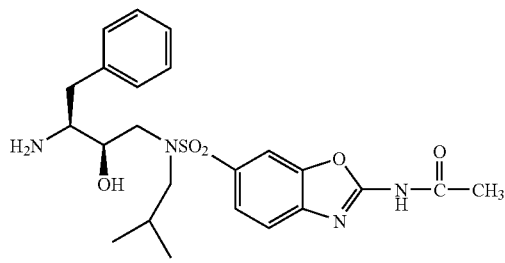

d) To a mixture of 1.1 g intermediate 3 and 364 mg triethylamine in dichloromethane was added 685 mg 1-[[[[(3R,3aS,6aR)-hexahydrofuro[2,3-b]furan-3-yl]oxy]carbonyl]-oxy]-2,5-pyrrolidinedione (described in WO9967417). This mixture is stirred at room temperature for 12 hours. After evaporation of dichloromethane under reduced pressure, the crude product is purified on silica. Thus, 900 mg of compound 1 was obtained with a yield of 59%.

EXAMPLE 2

Preparation of Compound 5 a) A mixture of 1 g of [(1S,2R)-2-hydroxy-3-[(2-methylpropyl)amino]-1-(phenyl-methyl)propyl]carbamic acid 1,1-dimethylethyl ester and 901 mg of triethylamine in 40 ml of dichloromethane was stirred at 0° C. Then 1 g of 2-(Ethoxycarbamoyl)-6-chlorosulfonylbenzoxazole was added and the reaction mixture stirred overnight at room temperature. After washing with sat NaHCO$_3$, the organic layer was separated, dried and evaporated, yielding 1.7 g (94%) of intermediate 4

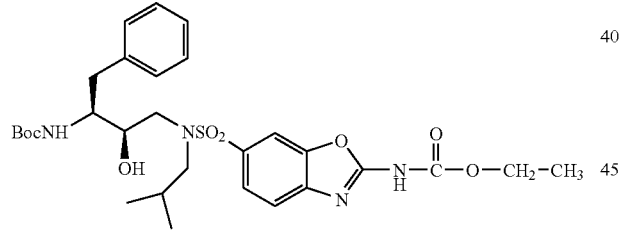

b) To a mixture of 1.7 g of intermediate 4 in 25 ml of dichloromethane, 3.2 g of trifluoracetic acid were added. The reaction mixture as stirred at room temperature for 6 hours. Extra dichloromethane was added and washed with NaHCO$_3$ solution. The organic layer was dried and evaporated under reduced pressure yielding 1.4 g (99%) of intermediate 5

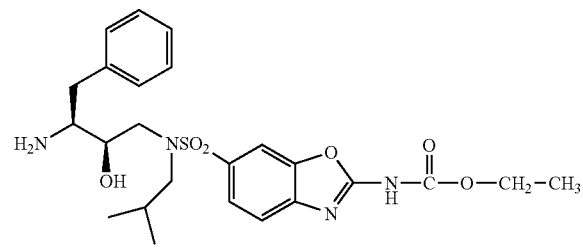

c) A mixture of 380 mg of intermediate 5, 107 mg of 1-hydroxybenzotriazole, 154 mg of 1-(3-dimethylaminopropyl)-3-ethylcarbodiimide hydrochloric acid and 143 mg of 2-(2,6-dimethylphenoxy)acetic acid in 20 ml of dichloromethane, was stirred overnight at room temperature. The reaction mixture was then washed with 5% HCl, saturated NaHCO$_3$ solution and brine. The organic layer was separated, dried and evaporated. The residue was purified by preparative-HPLC, yielding 141 mg (28%) of compound 5.

EXAMPLE 3

Preparation of Compound 3

To a mixture of 1.2 g intermediate 5 and 364 mg triethylamine in dichloromethane was added 685 mg 1-[[[[(3R,3aS,6aR)-hexahydrofuro[2,3-b]furan-3-yl]oxy]carbonyl]oxy]-2,5-pyrrolidinedione (described in WO9967417). This mixture is stirred at room temperature for 12 hours. After evaporation of dichloromethane under reduced pressure, the crude product is purified on silica, thus yielding 1.1 g (70%) of compound 3.

EXAMPLE 4

Preparation of Compound 2 a) To a mixture of 8 g β-[bis(phenylmethyl)amino]-α-[[(2-methylpropyl)amino]-methyl]-, (αR,βS)-benzenepropanol, prepared following the procedure in WO95/14653, and 3.2 g triethylamine in 150 ml dichloromethane was added at 0° C. 3.9 g 6-chlorosulfonyl-benzoxazolone (prepared as described in EP 0403947). After stirring for 24 hours at room temperature the reaction mixture was washed with sat. NaHCO$_3$, 8 g of intermediate 6:

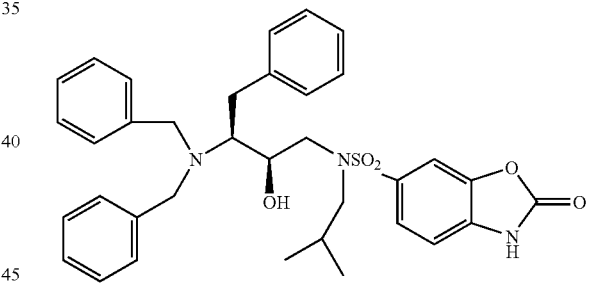

b) A mixture of 5.2 g intermediate 6 in 60 ml 10% NaOH-solution was heated to reflux overnight. After cooling the reaction mixture was acidified to pH=8 with 15% HCl. The aqueous phase was extracted two times with ethylacetate, yielding 3 g of intermediate 7:

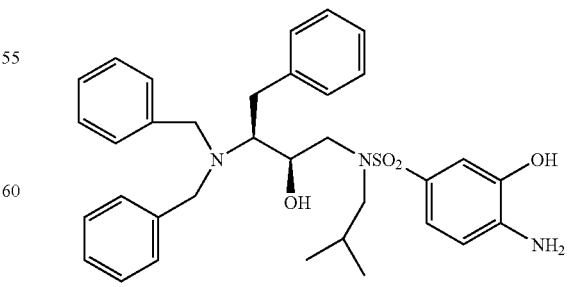

c) To a solution of 1.5 g intermediate 7 in ethanol was added 361 mg ethylpotassium xanthate. After refluxing this mixture for 16 hours, ethanol was removed under vacuum. To the residue was added H₂O. After acidification to pH=6 the precipitate was filtered of, yielding, after drying, 1.4 g of intermediate 8:

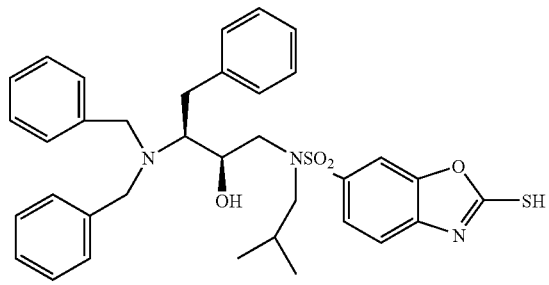

d) A mixture of 500 mg intermediate 8 and 70 mg N,N-dimethylethylenediamine in p-xylene was heated to 110° C. for 3 hours. After evaporation of the solvent and purification with column chromatography 181 mg of intermediate 9 was obtained:

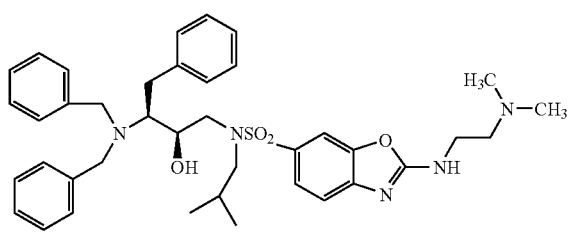

e) Debenzylation was performed with Pd/C and H₂ to afford intermediate 10.

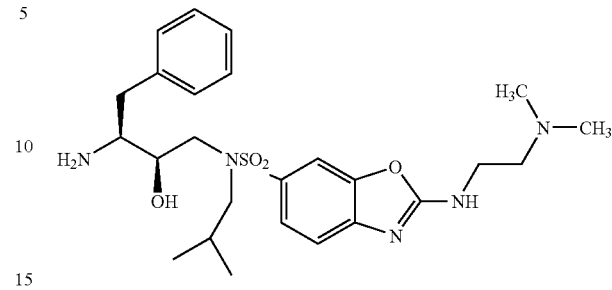

f) To a mixture of 95 mg intermediate 10 and 27 mg triethylamine in dichloromethane was added 51 mg 1-[[[[(3R, 3aS,6aR)-hexahydrofuro[2,3-b]furan-3-yl]oxy]carbonyl]-oxy]-2,5-pyrrolidinedione (described in W09967417). This mixture is stirred at room temperature for 12 hours. After evaporation of dichloromethane under reduced pressure, the crude product is purified on silica, yielding 83 mg of compound 2 (70%).

In an analogous way, compounds 4, 6, 7 and 8 were prepared.

EXAMPLE 5

Synthesis of Compound 10

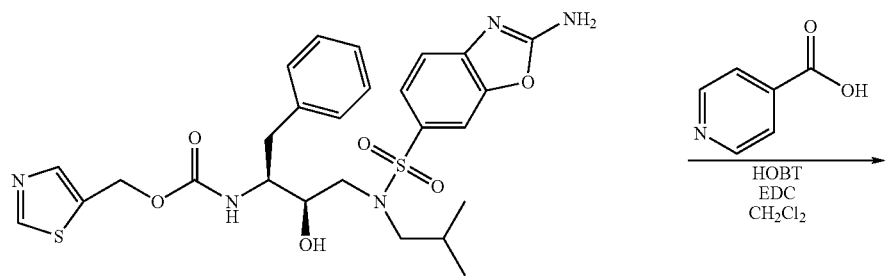

Intermediate 11

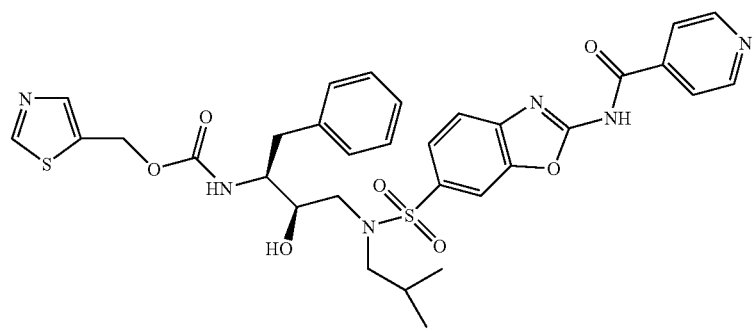

Compound 10

0.23 g of isonicotinic acid, 0.36 g of EDC and 12 mg of HOBT were mixed and added to 1 g of the 2-aminobenzoxazole intermediate 11 in 40 ml of dichloromethane. The mixture was stirred under an inert atmosphere of nitrogen at room temperature for 48 h. 50 ml of water was added the water layer was extracted with dichloromethane and the combined organic layers were washed with brine, dried under MgSO₄ and the solvent was evaporated under reduced pressure. Purification was performed on silica yielding 0.57 g (48%) of compound 10.

EXAMPLE 6

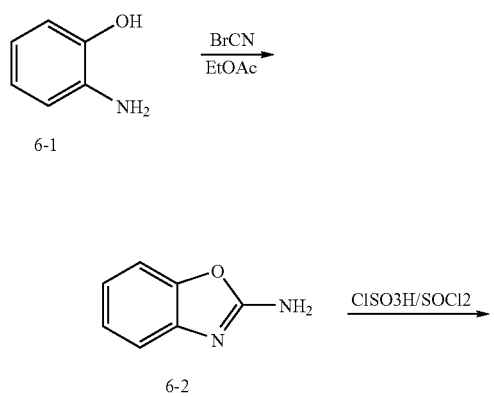

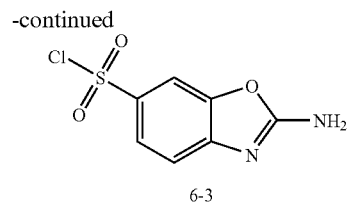

A mixture of 2.5 g 2-aminophenol (6-1) and 20 ml ethyl acetate was heated to 45° C. 3 g of cyanogen bromide was added to the mixture. The mixture was stirred at 45-50° C. for 12 hours. After cooling to room temperature, 1.5 g of sodium hydroxide in 15 ml of water was added. The organic layer was separated and washed with brine until neutral pH. Toluene (5 ml) was added and the solvent was removed to yield 2.71 g (88%) 2-aminobenzoxazol (6-2).

7.5 ml of chlorosulfonic acid was stirred at room temperature under an inert atmosphere. 5 g of 2-aminobenzoxazol (6-2) was added in small portions. The temperature was kept between 30-60° C. during the addition of 6-2. The mixture was heated to 80° C. for 2 hours. 5.3 g of thionyl chloride was added drop wise, keeping the temperature at 65° C. The mixture was stirred during 2 hours. After cooling to 0° C. 10 ml of ethyl acetate and 10 ml of a solution of sodium carbonate (1N) were added. The organic layer was separated from the water layer and this latter was extracted with ethyl acetate. The combined organic layers were dried over calcium chloride, yielding 7.8 g (90%) of 2-amino-6-chlorosulfonylbenzoxazole (6-3).

EXAMPLE 7

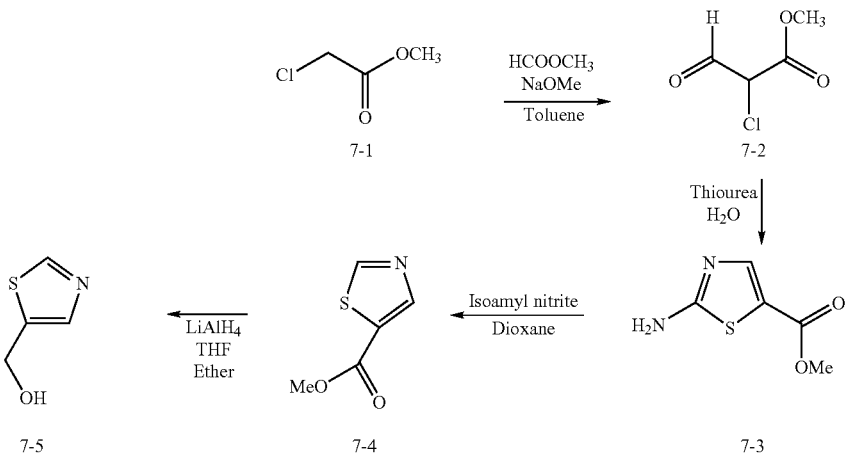

A mixture of 1 g of sodium methoxide and 10 ml of toluene was stirred at 0° C. under nitrogen atmosphere. A mixture of 1.9 g of methyl chloracetate (7-1) and 1.1 g of methylformate was added drop wise keeping the temperature between 5-10° C. The mixture was stirred for 2 hours at 0° C. After washing with water, the organic layer was dried and evaporated under reduced pressure yielding 2-chloro-3-oxo-propionic acid methyl ester (7-2).

A mixture of 2.4 g of 2-chloro-3-oxo-propionic acid methyl ester (7-2), water 20 ml and 1.75 g of thiourea was refluxed for 2 hours. The mixture was cooled to room temperature and 0.25 g of norit was added and filtered. A solution of 2.5N sodium hydroxide was added to the filtrate until neutral pH. The filtration yielded 1.23 g (44%) of 2-aminothiazole-5-carboxylic acid methyl ester (7-3).

The mixture of 2.15 g of isoamyl nitrite and 10 ml of dioxane was stirred at 80° C. under a nitrogen atmosphere. A solution of 1.23 g of 2-aminothiazole-5-carboxylic acid methyl ester (7-3) in 20 ml of dioxane was added drop wise. The mixture was refluxed for 2 hours. After cooling to room temperature 30 ml of ethyl acetate was added. The mixture was washed with brine and dried and the solvent evaporated under reduced pressure. The crude product is purified on silica, thus yielding 0.54 g (48%) of thiazol 5-carboxylic acid methyl ester (7-4).

A mixture of 0.54 g of thiazol 5-carboxylic acid methyl ester (g-4) and 10 ml tetrahydrofurane (THF) was stirred at 0° C. under a nitrogen atmosphere. The mixture of 0.16 g of lithium aluminium hydride and 5 ml of ether was added drop wise. After 1 hour at 0° C. water and 20% sodium hydroxide were added, and stirred during 30 minutes (min). The mixture was filtered over decalite and the solvent was removed by azeotropique distillation with toluene yielding 0.3g (69%) of thiazol-5-yl-methanol (7-5).

EXAMPLE 8

A mixture of 1.15 g of thiazol-5-yl-methanol (8-1) and 1.2 g triethylamine (TEA) in 25 ml of dichloromethane (DCM) was stirred at room temperature under an atmosphere of nitrogen. 2.56 g of N,N'-disuccinimidyl carbonate was then added and the resulting mixture was stirred for 10-15 minutes. The solution was stirred for an additional 2 hours. The resulting intermediate (8-2) was used directly in the subsequent reaction with the amine (8-3). Instead of amines also salts thereof can be used. Triethylamine 2 g and the amine 5 g (8-3) were added to dichloromethane 40 ml and the resulting mixture was stirred at room temperature. Subsequently, a portion of the solution comprising 8-2 was added drop wise. The reaction mixture was stirred at room temperature for 2 hours. The reaction mixture was washed with water and then dried to yield compound (8-4).

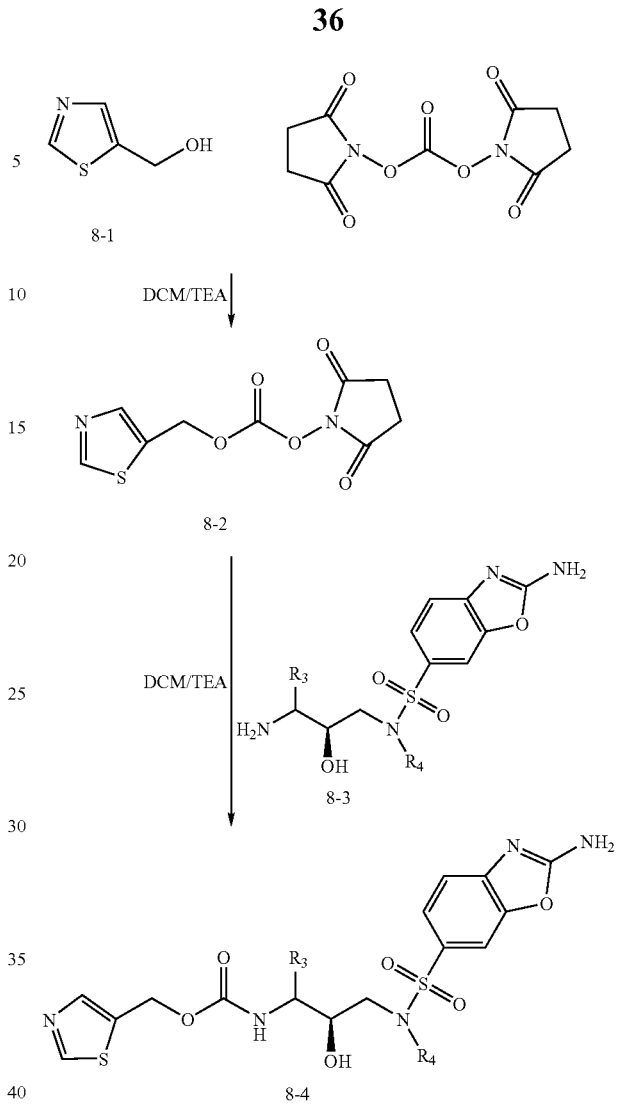

TABLE 1

Compounds of the present invention prepared according to the methods described above. If no stereochemistry is indicated, the compound is present as a racemic mixture.

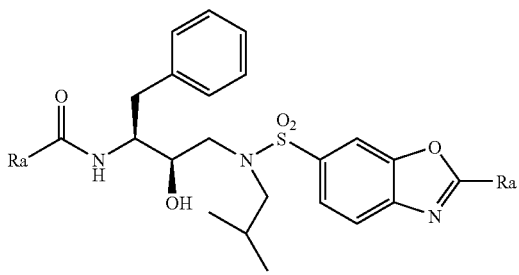

| Compound N° | $R_a$ | $R_b$ | Synthesis |
|---|---|---|---|
| 1 | (tetrahydrofuro-furanyl methoxy group) | —NHC(=O)CH$_3$ | A |

TABLE 1-continued

Compounds of the present invention prepared according to the methods described above. If no stereochemistry is indicated, the compound is present as a racemic mixture.

| Compound N° | R$_a$ | R$_b$ | Synthesis |
|---|---|---|---|
| 2 | hexahydrofuro[2,3-b]furan-3-yl (methoxy substituted) | —NHCH$_2$CH$_2$N(CH$_3$)$_2$ | B |
| 3 | hexahydrofuro[2,3-b]furan-3-yl (methoxy substituted) | —NHC(=O)OCH$_2$CH$_3$ | A |
| 4 | hexahydrofuro[2,3-b]furan-3-yl (methoxy substituted) | —NH—CH$_2$—CH$_2$—N(pyrrolidine) | B |
| 5 | 2,6-dimethylphenoxymethyl | —NHC(=O)OCH$_2$CH$_3$ | A |
| 6 | hexahydrofuro[2,3-b]furan-3-yl (methoxy substituted) | —NHCH$_2$CH$_2$OH | B |
| 7 | hexahydrofuro[2,3-b]furan-3-yl (methoxy substituted) | —N(CH$_3$)—CH$_2$—CH$_2$—N(pyrrolidine) | B |
| 8 | hexahydrofuro[2,3-b]furan-3-yl (methoxy substituted) | —N(CH$_3$)—CH$_2$—CH$_2$—N(pyrrolidine) | B |
| 9 | thiazol-5-ylmethoxy | —NHC(=O)OCH$_3$ | A |

TABLE 1-continued

Compounds of the present invention prepared according to the methods described above. If no stereochemistry is indicated, the compound is present as a racemic mixture.

| Compound N° | R$_a$ | R$_b$ | Synthesis |
|---|---|---|---|
| 10 | thiazol-5-yl-CH$_2$-O- | N-methyl isonicotinamide (pyridin-4-yl C(=O)NH-) | F |
| 11 | thiazol-5-yl-CH$_2$-O- | —NHC(=O)CH$_3$ | F |
| 12 | thiazol-5-yl-CH$_2$-O- | —NHC(=O)OCH$_2$CH$_3$ | A |
| 13 | thiazol-5-yl-CH$_2$-O- | 5-oxopyrrolidine-2-carboxamide | F |
| 14 | thiazol-5-yl-CH$_2$-O- | furan-2-carboxamide | F |
| 15 | thiazol-5-yl-CH$_2$-O- | 1-methylpiperidine-4-carboxamide | F |
| 16 | thiazol-5-yl-CH$_2$-O- | pyridine-2-carboxamide | F |
| 17 | thiazol-5-yl-CH$_2$-O- | 6-hydroxypyridine-3-carboxamide | F |

TABLE 1-continued

Compounds of the present invention prepared according to the methods described above. If no stereochemistry is indicated, the compound is present as a racemic mixture.

| Compound N° | R$_a$ | R$_b$ | Synthesis |
|---|---|---|---|
| 18 | thiazol-5-yl-CH$_2$-O-CH$_2$- | N-methyl nicotinamide derivative | F |
| 19 | thiazol-5-yl-CH$_2$-O-CH$_2$- | —NHC(=O)CH$_2$N(CH$_3$)$_2$ | B |
| 20 | thiazol-5-yl-CH$_2$-O-CH$_2$- | 4-methylpiperazin-1-yl | B |
| 21 | thiazol-5-yl-CH$_2$-O-CH$_2$- | piperazin-1-yl | B |
| 22 | thiazol-5-yl-CH$_2$-O-CH$_2$- | piperidin-1-yl | B |
| 23 | thiazol-5-yl-CH$_2$-O-CH$_2$- | pyrrolidin-1-yl | B |
| 24 | thiazol-5-yl-CH$_2$-O-CH$_2$- | N-methyl-N'-methyl-N'-(2-pyrrolidin-1-yl-ethyl)glycinamide | C |
| 25 | thiazol-5-yl-CH$_2$-O-CH$_2$- | 2-(4-methylpiperazin-1-yl)acetamide | C |
| 26 | thiazol-5-yl-CH$_2$-O-CH$_2$- | N-methyl-N-(pyridin-2-ylcarbonyl) | F |

TABLE 1-continued

Compounds of the present invention prepared according to the methods described above. If no stereochemistry is indicated, the compound is present as a racemic mixture.

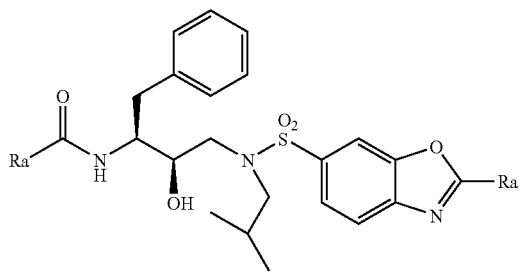

| Compound N° | $R_a$ | $R_b$ | Synthesis |
|---|---|---|---|
| 27 | thiazol-5-yl-CH$_2$-O- | N-methyl-N-(1-methylpiperidin-3-ylcarbonyl) | F |
| 28 | thiazol-5-yl-CH$_2$-O- | N-methyl-N-(1-methylpiperidin-4-ylcarbonyl) | F |
| 29 | thiazol-5-yl-CH$_2$-O- | N-methyl-N-(2-chloropyridin-4-ylcarbonyl) | F |
| 30 | thiazol-5-yl-CH$_2$-O- | N-methyl-N-(5-oxopyrrolidin-2-ylcarbonyl) | F |
| 31 | thiazol-5-yl-CH$_2$-O- | N-methyl-N-(pyridin-4-ylcarbonyl) | F |
| 32 | thiazol-5-yl-CH$_2$-O- | N-methyl-N-(pyridin-3-ylcarbonyl) | F |
| 33 | thiazol-5-yl-CH$_2$-O- | N-methyl-N-(furan-2-ylcarbonyl) | F |

TABLE 1-continued

Compounds of the present invention prepared according to the methods described above. If no stereochemistry is indicated, the compound is present as a racemic mixture.

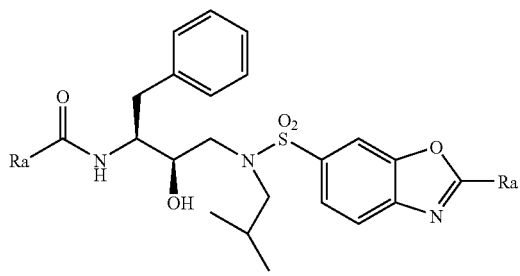

| Compound N° | $R_a$ | $R_b$ | Synthesis |
|---|---|---|---|
| 34 | thiazole-CH₂-O- | -NH-C(O)-pyrrolidinyl-N-CH₃ | F |
| 35 | thiazole-CH₂-O- | -NH-C(O)-(S)-pyrrolidinyl-N-CH₃ | F |
| 36 | thiazole-CH₂-O- | -N(CH₃)-CH₂-CH₂-pyrrolidinyl | B |
| 37 | thiazole-CH₂-O- | -NH-CH₂-C(O)-pyrrolidinyl-N-CH₃ | F |

Antiviral Analyses:

The compounds of the present invention were examined for anti-viral activity in a cellular assay. The assay demonstrated that these compounds exhibited potent anti-HIV activity against a wild type laboratory HIV strain (HIV-1 strain LAI). The cellular assay was performed according to the following procedure.

Cellular Assay Experimental Method:

HIV- or mock-infected MT4 cells were incubated for five days in the presence of various concentrations of the inhibitor. At the end of the incubation period, all HIV-infected cells have been killed by the replicating virus in the control cultures in the absence of any inhibitor. Cell viability is measured by measuring the concentration of MTT, a yellow, water soluble tetrazolium dye that is converted to a purple, water insoluble formazan in the mitochondria of living cells only. Upon solubilization of the resulting formazan crystals with isopropanol, the absorbance of the solution is monitored at 540 nm. The values correlate directly to the number of living cells remaining in the culture at the completion of the five day incubation. The inhibitory activity of the compound was monitored on the virus-infected cells and was expressed as $EC_{50}$ and $EC_{90}$. These values represent the amount of the compound required to protect 50% and 90%, respectively, of the cells from the cytopathogenic effect of the virus. The toxicity of the compound was measured on the mock-infected cells and was expressed as $CC_{50}$, which represents the concentration of compound required to inhibit the growth of the cells by 50%. The selectivity index (SI) (ratio $CC_{50}/EC_{50}$) is an indication of the selectivity of the anti-HIV activity of the inhibitor. Wherever results are reported as e.g. $pEC_{50}$ or $pCC_{50}$ values, the result is expressed as the negative logarithm of the result expressed as $EC_{50}$ or $CC_{50}$ respectively.

Antiviral Spectrum:

Because of the increasing emergence of drug resistant HIV strains, the present compounds were tested for their potency against clinically isolated HIV strains harboring several mutations (Table 2 and 3). These mutations are associated with resistance to protease inhibitors and result in viruses that show various degrees of phenotypic cross-resistance to the currently commercially available drugs such as for instance saquinavir, ritonavir, nelfinavir, indinavir and amprenavir.

TABLE 2

List of mutations present in the protease gene of the HIV strains (A to F) used.

| | |
|---|---|
| A | V003I, L010I, V032T, L033M, E035D, S037Y, S037D, M046I, R057R/K, Q058E, L063P, K070T, A071V, I072V, I084V, L089V |
| B | V003I, L010I, K020R, E035D, M036I, S037N, Q058E, I062V, L063P, A071V, I072M, G073S, V077I, I084V, I085V, L090M |
| C | V003I, L010I, I015V, L019I, K020M, S037N, R041K, I054V, Q058E, L063P, A071V, I084V, L090M, I093L |
| D | V003I, L010L/I, I013V, L033I, E035D, M036I, M046L, K055R, R057K, L063P, I066F, A071V, I084V, N088D, L090M |
| E | V003I, L010I, V011I, A022V, L024I, E035D, M036I, S037T, R041K, I054V, I062V, L063P, A071V, I084V |
| F | L010F, M046I, M071V, I084V |

Results:

As a measure of the broad spectrum activity of the present compounds, the fold resistance (FR), defined as FR=$EC_{50}$ (mutant strain)/$EC_{50}$(HIV-1 strain LAI), was determined. Table 3 shows the results of the antiviral testing in terms of fold resistance. As can be seen in this table, the present compounds are effective in inhibiting a broad range of mutant strains: Column A FR value towards mutant A, Column B: FR towards mutant B , Column C: FR towards mutant C, Column D: FR towards mutant D, Column E: FR towards mutant E, Column F: FR towards mutant F. The toxicity is expressed as the $pCC_{50}$ value as determined with mock transfected cells.

TABLE 3

Results of the toxicity testing and the resistance testing against strain A to F (expressed as FR).

| Comp. N° | Tox | A (FR) | B (FR) | C (FR) | D (FR) | E (FR) | F (FR) |
|---|---|---|---|---|---|---|---|
| 1 | <4 | 0.63 | 0.80 | 0.50 | 0.72 | 0.40 | 0.71 |
| 2 | <4 | 1.1 | 0.49 | 0.59 | 0.32 | 0.36 | 2.7 |
| 3 | 4.24 | 0.74 | 0.66 | 0.59 | 0.40 | 0.35 | 1.1 |
| 4 | ND | 1.95 | 1.62 | 1.70 | 0.47 | 0.50 | 3.2 |
| 5 | 5.04 | 3.1 | 1.1 | 2.63 | 2.1 | 1.64 | 16 |
| 7 | 4.49 | 13 | ND | 0.70 | ND | 2.3 | 30 |
| 8 | <4 | 30 | 5.8 | 1.7 | 5.8 | ND | 58 |
| 9 | <4 | 3.5 | 1.2 | 1.2 | 2.7 | 3.6 | 14.5 |
| 10 | 4.27 | 3.9 | 10.83 | 1.1 | 3.9 | 1.3 | 20 |
| 11 | <4 | 42 | 2.1 | 2.5 | 10 | 4.8 | 74 |
| 12 | <4 | 8.5 | 1.4 | 2.5 | 4.8 | 2.5 | 15 |
| 13 | <4 | 2.3 | 0.75 | 0.64 | 0.91 | 0.91 | 5.2 |
| 14 | 5.03 | 5.2 | 3.8 | 3.1 | 3.7 | 3.1 | 19 |
| 15 | <4 | 2.3 | 0.81 | 1.1 | 1.7 | 1.5 | 7.8 |
| 16 | 4.25 | 3.5 | 0.72 | 0.69 | 3.3 | 1.1 | 17 |
| 17 | <4 | 3.1 | 0.79 | 0.91 | 3.1 | 1.7 | 13 |
| 18 | 4.24 | 2.6 | 0.85 | 1.5 | 3.0 | 2.6 | 13 |
| 19 | <4 | 3.0 | 0.81 | 0.91 | 2.2 | ND | 17 |
| 24 | <4 | 1.9 | 0.53 | 1.3 | 1.6 | 1.4 | 6.8 |
| 25 | 4.31 | 3.9 | 1.3 | 3.0 | 3.9 | 3.9 | 18 |
| 26 | 4.14 | 9.3 | 2.45 | 3.4 | 15 | 11 | 59 |
| 27 | <4 | 4.4 | 1.00 | 0.68 | 2.9 | 0.85 | 24 |
| 28 | <4 | 4.4 | 0.89 | 0.51 | 2.9 | 1.9 | 23 |
| 29 | <4 | 8.1 | 1.4 | 0.79 | 4.9 | 0.87 | 39 |
| 30 | <4 | ND | ND | ND | ND | ND | ND |
| 31 | <4 | 9.5 | 1.3 | 1.25 | 7.6 | ND | 33 |
| 32 | <4 | 8.3 | 1.7 | 1.1 | 8.1 | ND | 42 |
| 34 | 4.25 | 7.2 | 1.4 | 1.7 | 5.8 | 2.3 | 25 |
| 35 | 4.26 | 13 | 2.3 | 1.1 | 3.5 | ND | 48 |

ND indicates not determined

Biovailability:

Caco-2 Permeability Assay for Intestinal Absorption

The permeability of different compounds is evaluated according to a Caco-2 test protocol as described by Augustijns et al. (Augustijns et al. (1998). *Int. J. of Pharm*, 166, 45-54) whereby, Caco-2 cells at cell passage number between 32 and 45 are grown in 24-well transwell cell culture plates for 21 to 25 days. The integrity of the cell monolayer is checked by measuring the transepithelial electrical resistance (TEER). The test is performed at pH 7.4 and at 100 µM donor compound concentration.

Aqueous Solubility at Different pH Levels

The equilibrium solubility in simulated gastrointestinal solutions under thermodynamic conditions is a good measure for the solubility profile of the compound in the stomach and the different parts of the intestine. Simulated gastric fluid (SGF) (without pepsin) is set at pH of 1.5. Simulated intestinal fluids (SIF) (without bile salts) are set at pH 5, pH 6.5, pH 7 and pH 7.5. The experimental protocol uses 96-well flat-bottom microplates in which 1 mg of compound is added per well (stock solution in methanol) and evaporated to dryness. The compounds are resolubilized in SGF and SIF and incubated overnight on a horizontal shaking device at 37° C. After filtration, the compound concentrations are determined by UV-spectrophotometry.

Oral Availability in the Rat

The compounds are formulated as a 20 mg/ml solution or suspension in DMSO, PEG400 or cyclodextin 40% in water. For most experiments in the rat (male and female rats), three dosing groups are formed: 1/single intraperitoneal (IP) dose at 20 mg/kg using the DMSO formulation; 2/single oral dose at 20 mg/kg using the PEG400 formulation and 3/single oral dose at 20 mg/kg using the cyclodextrin formulation. Blood is sampled at regular time intervals after dosing and drug concentrations in the serum are determined using a LC-MS bioanalytical method. Serum concentrations are expressed in ng/mg after normalization to 10 mg/kg. Serum concentration at 30 minutes (30') and at 3 hours (180') can be determined as these values reflect the extent of absorption (30') and the speed of elimination (180'). The rat serum concentration at 30 min and 180 min following IP administration of 20 mg/kg of compound 4 are 1098 ng/ml and 553 ng/ml respectively.

Boosting the Systemic Bioavailability

With the described type of compounds (protease-inhibitors), it is known that inhibition of the metabolic degradation processes can markedly increase the systemic availability by reducing the first-pass metabolism in the liver and the metabolic clearance from the plasma. This 'boosting' principle can be applied in a clinical setting to the pharmacological action of the drug. This principle can be also explored both in the rat or the dog by simultaneous administration of a compound that inhibits the Cyt-p450 metabolic enzymes. Known blockers are for example ritonavir and ketoconazole. Dosing a single oral dose of ritonvir at 5 mg/kg in the rat and the dog may result in an increase of the systemic availability.

Protein Binding Analyses:

Human serum proteins like albumin (HSA) or α-1 acid glycoprotein (AAG) are known to bind many drugs, resulting in a possible decrease in the effectiveness of those compounds. In order to determine whether the present compounds would be adversely affected by this binding, the anti-HIV activity of the compounds was measured in the presence of human serum, thus evaluating the effect of the binding of the protease inhibitors to those proteins.

MT4 cells are infected with HIV-1 LAI at a multiplicity of infection (MOI) of 0.001-0.01 $CCID_{50}$ (50% cell culture infective dose per cell, $CCID_{50}$). After 1 h incubation, cells are washed and plated into a 96 well plate containing serial dilutions of the compound in the presence of 10% FCS (foetal calf serum), 10% FCS+1 mg/ml AAG ($\alpha_1$-acid glycoprotein), 10% FCS+45 mg/ml HSA (human serum albumin) or 50% human serum (HS). After 5 or 6 days incubation, the $EC_{50}$ (50% effective concentration in cell-based assays) is calculated by determining the cell viability or by quantifying the level of HIV replication. Cell viability is measured using the assay described above. Into a 96 well plate containing serial dilutions of the compound in the presence of 10% FCS or 10% FCS+1 mg/ml AAG, HIV (wild type or resistant strain) and MT4 cells are added to a final concentration of 200-250 $CCID_{50}$/well and 30,000 cells/well, respectively. After 5 days of incubation (37° C., 5% $CO_2$), the viability of the cells is determined by the tetrazolium colorimetric MTT (3-[4,5-Dimethylthiazol-2-yl]-2,5-diphenyltetrazolium bromide) method (Pauwels et al. J Virol. Methods 1988, 20, 309-321).

TABLE 4

Effect of the protein binding on the in vitro activity of compound 1

| Compound name | Ratio of the $EC_{50}$ compared to FCS (10%) | | | |
| --- | --- | --- | --- | --- |
| | FCS (10%) | AAG 1 mg/ml | HSA 45 mg/ml | HS 50% |
| Compound 1 | 1 | 25 | 6 | 15 |

The invention claimed is:

1. A method of inhibiting a protease of a retrovirus in a mammal infected with said retrovirus, said method comprising administering a protease inhibiting amount of a compound having the formula

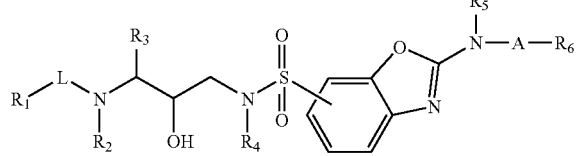

(I)

an N-oxide, salt, stereoisomeric form, racemic mixture, prodrug, thereof, wherein $R_1$ and $R_8$ are, each independently, hydrogen, $C_{1-6}$alkyl, $C_{2-6}$alkenyl, aryl$C_{1-6}$alkyl, $C_{3-7}$cycloalkyl, $C_{3-7}$cycloalkyl$C_{1-6}$alkyl, aryl, $Het^1$, $Het^1C_{1-6}$alkyl, $Het^2$, $Het^2C_{1-6}$alkyl;

$R_1$ may also be a radical of formula

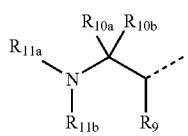

(II)

wherein $R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, $Het^1$, $Het^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(=O)$_t$, hydroxy, cyano, halogen or amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl; wherein $R_9$, $R_{10a}$ and the carbon atoms to which they are attached may also form a $C_{3-7}$cycloalkyl radical; when L is —O—$C_{1-6}$alkanediyl-C(=O)— or —$NR_8$-$C_{1-6}$alkanediyl-C(=O)—, then $R_9$ may also be oxo;

$R_{11a}$ is hydrogen, $C_{2-6}$alkenyl, $C_{2-6}$alkynyl, $C_{3-7}$cycloalkyl, aryl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, $Het^1$oxycarbonyl, $Het^2$oxycarbonyl, aryloxycarbonyl$C_{1-4}$alkyl, aryl$C_{1-4}$alkyloxycarbonyl, $C_{1-4}$alkylcarbonyl, $C_{3-7}$cycloalkylcarbonyl, $C_{3-7}$cycloalkyl $C_{1-4}$alkyloxycarbonyl, $C_{3-7}$cycloalkylcarbonyloxy, carboxyl$C_{1-4}$alkylcarbonyloxy, $C_{1-4}$alkylcarbonyloxy, aryl$C_{1-4}$alkylcarbonyloxy, arylcarbonyloxy, aryloxycarbonyloxy, $Het^1$carbonyl, $Het^1$carbonyloxy, $Het^1C_{1-4}$alkyloxycarbonyl, $Het^2$carbonyloxy, $Het^2C_{1-4}$alkylcarbonyloxy, $Het^2C_{1-4}$alkyloxycarbonyloxy or $C_{1-4}$alkyl optionally substituted with aryl, aryloxy, $Het^2$, halogen or hydroxy; wherein the substituents on the amino groups are each independently selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl;

$R_{11b}$ is hydrogen, $C_{3-7}$cycloalkyl, $C_{2-6}$alkenyl, $C_{2-6}$alkynyl, aryl, $Het^1$, $Het^2$ or $C_{1-4}$alkyl optionally substituted with halogen, hydroxy, $C_{1-4}$alkylS(=O)$_t$, aryl, $C_{3-7}$cycloalkyl, $Het^1$, $Het^2$, amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl; wherein $R_{11b}$ may be linked to the remainder of the molecule via a sulfonyl group;

each independently, t is zero, 1 or 2;

$R_2$ is hydrogen or $C_{1-6}$alkyl;

L is —C(=O)—, —O—C(=O)—, —$NR_8$—C(=O)—, —O—$C_{1-6}$alkanediyl-C(=O)—, —$NR_8$—$C_{1-6}$alkanediyl-C(=O)—, —S(=O)$_2$—, —O—S(=O)$_2$—, —$NR_8$—S(=O)$_2$ wherein either the C(=O) group or the S(=O)$_2$ group is attached to the $NR_2$ moiety; wherein the $C_{1-6}$alkanediyl moiety is optionally substituted with aryl, $Het^1$ or $Het^2$;

$R_3$ is $C_{1-6}$alkyl, aryl, $C_{3-7}$cycloalkyl, $C_{3-7}$cycloalkyl $C_{1-4}$alkyl, or aryl$C_{1-4}$alkyl;

$R_4$ is hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl, or $C_{1-6}$alkyl optionally substituted with one or more substituents each independently selected from aryl, $Het^1$, $Het^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(=O)$_t$, hydroxy, cyano, halogen and amino optionally mono- or disubstituted where the substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl;

A is $C_{1-6}$alkanediyl, —C(=O)—, —C(=S)—, —S(=O)$_2$—, $C_{1-6}$alkanediyl-C(=O)—, $C_{1-6}$alkanediyl-C (=S)— or $C_{1-6}$alkanediyl-S(=O)$_2$—; wherein the point of attachment to the nitrogen atom is the $C_{1-6}$alkanediyl group in those moieties containing said group;

$R_5$ is hydrogen, hydroxy, $C_{1-6}$alkyl, Het$^1C_{1-6}$alkyl, Het$^2C_{1-6}$alkyl, amino$C_{1-6}$alkyl wherein the amino group may optionally be mono- or di-substituted with $C_{1-4}$alkyl;

$R_6$ is $C_{1-6}$alkyloxy, Het$^1$, Het$^1$oxy, Het$^2$, Het$^2$oxy, aryl, aryloxy or amino; and in case -A- is other than $C_{1-6}$alkanediyl then $R_6$ may also be $C_{1-4}$alkyl, Het$^1C_{1-4}$alkyl, Het$^1$oxy$C_{1-4}$alkyl, Het$^2C_{1-4}$alkyl, Het$^2$oxy$C_{1-4}$alkyl, aryl$C_{1-4}$alkyl, aryloxy$C_{1-4}$alkyl or amino$C_{1-6}$alkyl; wherein each of the amino groups in the definition of $R_6$ may optionally be substituted with one or more substituents each independently selected from $C_{1-4}$alkyl, $C_{1-4}$alkylcarbonyl, $C_{1-4}$alkyloxycarbonyl, aryl, arylcarbonyl, aryloxycarbonyl, Het$^1$, Het$^2$, aryl$C_{1-4}$alkyl, Het$^1C_{1-4}$alkyl and Het$^2C_{1-4}$alkyl; and -A-$R_6$ may also be hydroxy$C_{1-6}$alkyl;

$R_5$ and A-$R_6$ taken together with the nitrogen atom to which they are attached may also form Het$^1$ or Het$^2$;

to said mammal in need thereof.

2. The method of claim 1, wherein said mammal is a human.

3. The method as claimed in claim 1, wherein the HIV virus is a multi-drug resistant strain.

4. A method of inhibiting a protease of a retrovirus in a mammal infected with said retrovirus, said method comprising administering a protease inhibiting amount of a compound selected from the group consisting of compounds of the following formula:

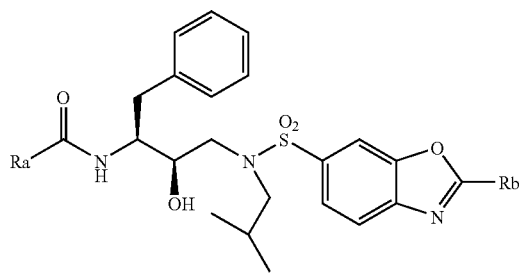

wherein R$_a$ is 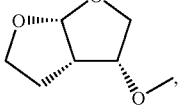 and R$_b$ is —NHC(=O)CH$_3$;

wherein R$_a$ is 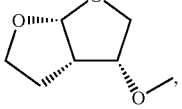 and R$_b$ is —NHCH$_2$CH$_2$N(CH$_3$)$_2$;

wherein R$_a$ is 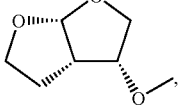 and R$_b$ is —NHC(=O)OCH$_2$CH$_3$;

wherein R$_a$ is 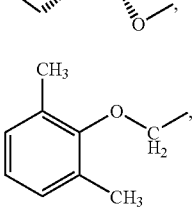 and R$_b$ is wherein R$_a$ is 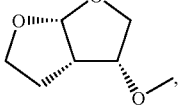 and R$_b$ is —NHC(=O)OCH$_2$CH$_3$;

wherein R$_a$ is 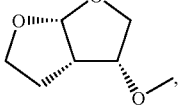 and R$_b$ is —NHCH$_2$CH$_2$OH;

-continued
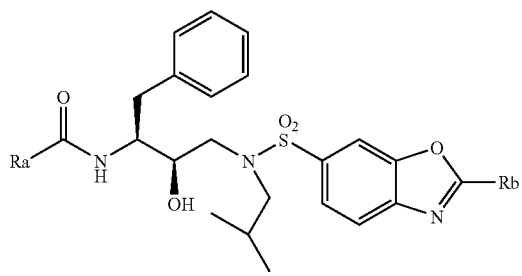
| | | |
|---|---|---|
| wherein R$_a$ is 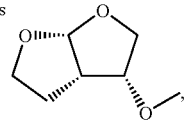 | and R$_b$ is 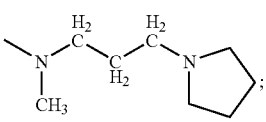 | |
| wherein R$_a$ is 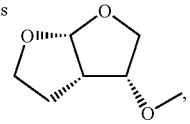 | and R$_b$ is 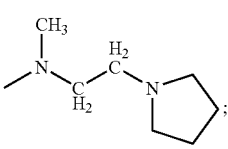 | |
| wherein R$_a$ is 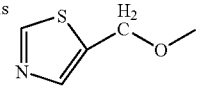 | and R$_b$ is —NHC(=O)OCH$_3$; | |
| wherein R$_a$ is 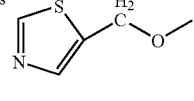 | and R$_b$ is 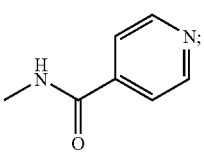 | |
| wherein R$_a$ is 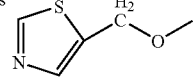 | and R$_b$ is —NHC(=O)CH$_3$; | |
| wherein R$_a$ is 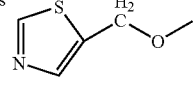 | and R$_b$ is —NHC(=O)OCH$_2$CH$_3$; | |
| wherein R$_a$ is 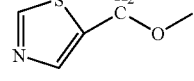 | and R$_b$ is 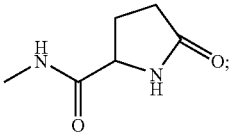 | |
| wherein R$_a$ is 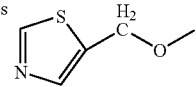 | and R$_b$ is 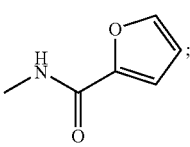 | |
| wherein R$_a$ is 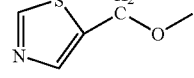 | and R$_b$ is 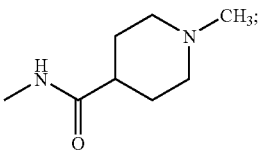 | |

-continued
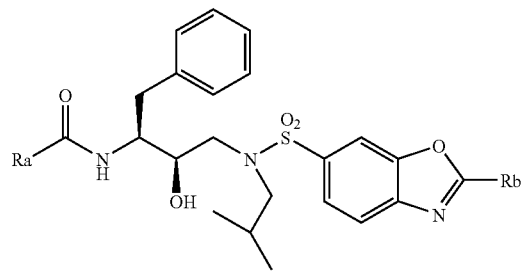
| | | |
|---|---|---|
| wherein R$_a$ is | 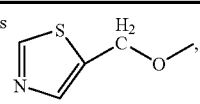 | and R$_b$ is 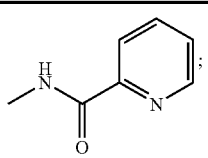; |
| wherein R$_a$ is | 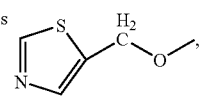 | and R$_b$ is 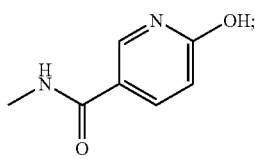; |
| wherein R$_a$ is | 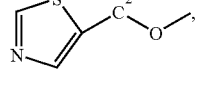 | and R$_b$ is 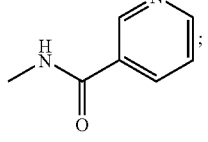; |
| wherein R$_a$ is | 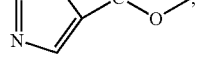 | and R$_b$ is —NHC(=O)CH$_2$N(CH$_3$)$_2$; |
| wherein R$_a$ is | 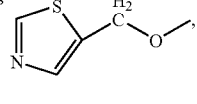 | and R$_b$ is 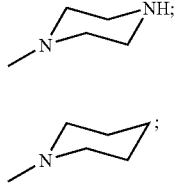; |
| wherein R$_a$ is | 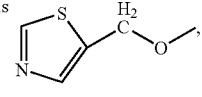 | and R$_b$ is 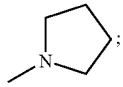; |
| wherein R$_a$ is | 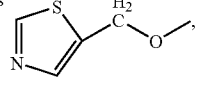 | and R$_b$ is 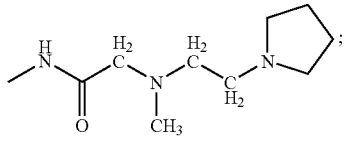; |
| wherein R$_a$ is | 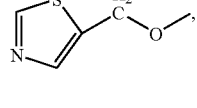 | and R$_b$ is 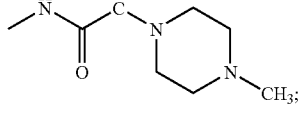; |

-continued
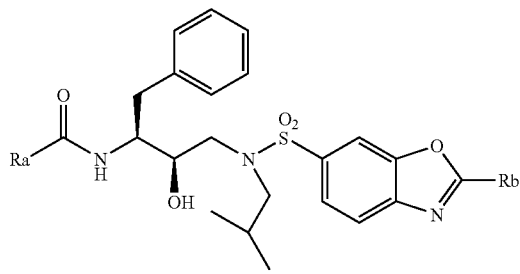
| | | | |
|---|---|---|---|
| wherein R$_a$ is | 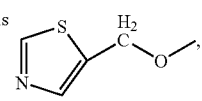 | and R$_b$ is | 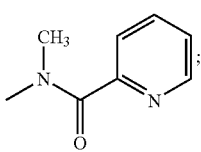; |
| wherein R$_a$ is | 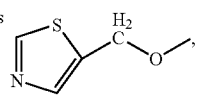 | and R$_b$ is | 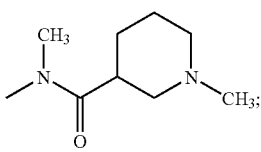; |
| wherein R$_a$ is | 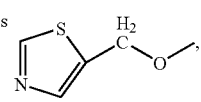 | and R$_b$ is | 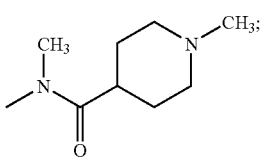; |
| wherein R$_a$ is | 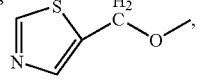 | and R$_b$ is | 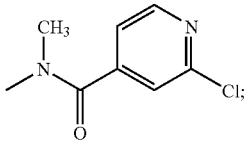; |
| wherein R$_a$ is | 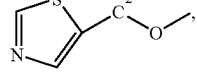 | and R$_b$ is | 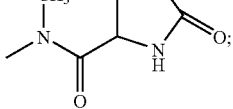; |
| wherein R$_a$ is | 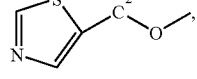 | and R$_b$ is | 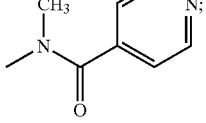; |
| wherein R$_a$ is | 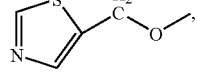 | and R$_b$ is | 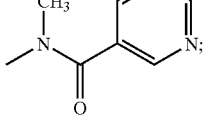; |
| wherein R$_a$ is | 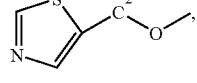 | and R$_b$ is | 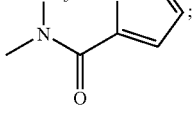; |

-continued

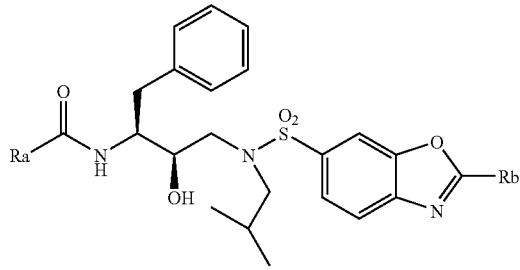

wherein $R_a$ is 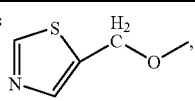 and $R_b$ is 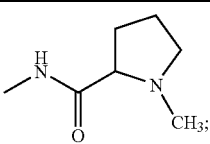

wherein $R_a$ is 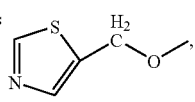 and $R_b$ is 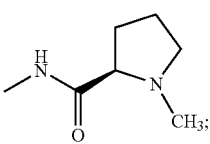

wherein $R_a$ is 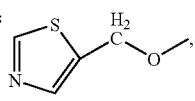 and $R_b$ is 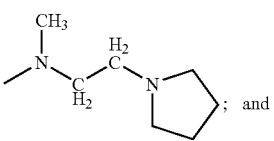; and

N-oxides, salts, stereoisomeric forms, racemic mixtures, and prodrug, thereof; to said mammal in need thereof.

5. The method of claim 4, wherein said mammal is a human.

6. The method as claimed in claim 5, wherein the HIV virus is a multi-drug resistant strain.

7. The method of claim 1, wherein:

$R_9$, $R_{10a}$ and $R_{10b}$ are, each independently, hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl or $C_{1-4}$alkyl optionally substituted with aryl, Het$^1$, Het$^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(O)$_t$, hydroxy, cyano, halogen or amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1$$C_{1-4}$alkyl and Het$^2$$C_{1-4}$alkyl; wherein $R_9$, $R_{10a}$ and the carbon atoms to which they are attached may also form a $C_{3-7}$cycloalkyl radical;

$R_{11a}$ is hydrogen, $C_{2-6}$alkenyl, $C_{2-6}$alkynyl, $C_{3-7}$cycloalkyl, aryl, aminocarbonyl optionally mono- or disubstituted, amino$C_{1-4}$alkylcarbonyloxy optionally mono- or disubstituted, $C_{1-4}$alkyloxycarbonyl, aryloxycarbonyl, Het$^1$oxycarbonyl, Het$^2$oxycarbonyl, aryloxycarbonyl$C_{1-4}$alkyl, aryl$C_{1-4}$alkyloxycarbonyl, $C_{1-4}$alkylcarbonyl, $C_{3-7}$cycloalkylcarbonyl, $C_{3-7}$cycloalkyl$C_{1-4}$alkyloxycarbonyl, $C_{3-7}$cycloalkylcarbonyloxy, carboxyl$C_{1-4}$alkylcarbonyloxy, $C_{1-4}$alkylcarbonyloxy, aryl$C_{1-4}$alkylcarbonyloxy, arylcarbonyloxy, aryloxycarbonyloxy, Het$^1$carbonyl, Het$^1$carbonyloxy, Het$^1$$C_{1-4}$alkyloxycarbonyl, Het$^2$carbonyloxy, Het$^2$$C_{1-4}$alkylcarbonyloxy, Het$^2$$C_{1-4}$alkyloxycarbonyloxy or $C_{1-4}$alkyl optionally substituted with aryl, aryloxy, Het$^2$ or hydroxy; wherein the substituents on the amino groups are each independently selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1$$C_{1-4}$alkyl and Het$^2$$C_{1-4}$alkyl;

$R_{11b}$ is hydrogen, $C_{3-7}$cycloalkyl, $C_{2-6}$alkenyl, $C_{2-6}$alkynyl, aryl, Het$^1$, Het$^2$ or $C_{1-4}$alkyl optionally substituted with halogen, hydroxy, $C_{1-4}$alkylS(=O)$_t$, aryl, $C_{3-7}$cycloalkyl, Het$^1$, Het$^2$, amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1$$C_{1-4}$alkyl and Het$^2$$C_{1-4}$alkyl; wherein $R_{11b}$ may be linked to the remainder of the molecule via a sulfonyl group;

t is zero, 1 or 2;

L is —C(=O)—, —O—C(=O)—, —NR$_8$—C(=O)—, —O—$C_{1-6}$alkanediyl-C(=O)—, —NR$_8$-$C_{1-6}$alkanediyl-C(=O)—, —S(=O)$_2$—, —O—S(=O)$_2$—, —NR—S(=O)$_2$ wherein either the C(=O) group or the S(=O)$_2$ group is attached to the NR$_2$ moiety;

$R_4$ is hydrogen, $C_{1-4}$alkyloxycarbonyl, carboxyl, aminocarbonyl, mono- or di($C_{1-4}$alkyl)aminocarbonyl, $C_{3-7}$cycloalkyl, $C_{2-6}$alkenyl, $C_{2-6}$alkynyl, or $C_{1-6}$alkyl optionally substituted with one or more substituents selected from aryl, Het$^1$, Het$^2$, $C_{3-7}$cycloalkyl, $C_{1-4}$alkyloxycarbonyl, carboxyl, aminocarbonyl, mono- or di($C_{1-4}$alkyl)aminocarbonyl, aminosulfonyl, $C_{1-4}$alkylS(=O)$_t$, hydroxy, cyano, halogen and amino optionally mono- or disubstituted where the substituents are selected from $C_{1-4}$alkyl, aryl, aryl$C_{1-4}$alkyl, $C_{3-7}$cycloalkyl, $C_{3-7}$cycloalkyl$C_{1-4}$alkyl, Het$^1$, Het$^2$, Het$^1$$C_{1-4}$alkyl and Het$^2$$C_{1-4}$alkyl; and $R_6$ is $C_{1-6}$alkyloxy, Het$^1$, Het$^1$oxy, Het$^2$, Het$^2$oxy, aryl, aryloxy or amino; and in case -A- is other than $C_{1-6}$alkanediyl then $R_6$ may also be $C_{1-6}$alkyl, $Het^1C_{1-4}$alkyl, $Het^1oxyC_{1-4}$alkyl, $Het^2C_{1-4}$alkyl, $Het^2oxyC_{1-4}$alkyl, $arylC_{1-4}$alkyl, $aryloxyC_{1-4}$alkyl or $aminoC_{1-4}$alkyl; wherein each of the amino groups in the definition of $R_6$ may optionally be substituted with one or more substituents selected from $C_{1-4}$alkyl, $C_{1-4}$alkylcarbonyl, $C_{1-4}$alkyloxycarbonyl, aryl, arylcarbonyl, aryloxycarbonyl, $Het^1$, $Het^2$, $arylC_{1-4}$alkyl, $Het^1 C_{1-4}$alkyl and $Het^2C_{1-4}$alkyl.

8. The method of claim 1, wherein:
$R_1$ is hydrogen, $C_{1-6}$alkyl, $C_{2-6}$alkenyl, $arylC_{1-6}$alkyl, $C_{3-7}$cycloalkyl, $C_{3-7}$cycloalkyl$C_{1-6}$alkyl, aryl, $Het^1$, $Het^1C_{1-6}$alkyl, $Het^2$ or $Het^2C_{1-6}$alkyl; wherein $Het^1$ is a saturated or partially unsaturated monocyclic heterocycle having 5 or 6 ring members, which contains one or more heteroatom ring members each independently selected from nitrogen, oxygen and sulfur and which is optionally substituted on one or more carbon atoms.

9. The method of claim 1, wherein:
L is —O—$C_{1-6}$alkanediyl-C(=O)—.

10. The method of claim 1, wherein:
A is $C_{1-6}$alkanediyl, —C(=O)— or $C_{1-6}$alkanediyl-C(=O)—; wherein the point of attachment to the nitrogen atom is the $C_{1-6}$alkanediyl group in those moieties containing said group;
$R_5$ is hydrogen, $C_{1-6}$alkyl, $Het^1C_{1-6}$alkyl, $Het^2C_{1-6}$alkyl, $aminoC_{1-6}$alkyl wherein the amino group may optionally be mono- or di-substituted with $C_{1-4}$alkyl; and
in case -A- is —C(=O)— then $R_{1-6}$ is $C_{1-6}$alkyloxy, $Het^1$, $Het^1oxy$ or $Het^2oxy$, aryl, $Het^1C_{1-4}$alkyl, $Het^1oxyC_{1-4}$alkyl, $Het^2C_{1-4}$alkyl, $Het^2oxyC_{1-4}$alkyl, $arylC_{1-4}$alkyl, $aryloxyC_{1-4}$alkyl or $aminoC_{1-4}$alkyl; and
in case -A- is $C_{1-6}$alkanediyl then $R_6$ is amino, $C_{1-6}$alkyloxy, $Het^1$, $Het^1oxy$ or $Het^2oxy$; and
in case -A- is $C_{1-6}$alkanediyl-C(=O)— then $R_6$ is $C_{1-6}$alkyloxy, $Het^1$, $Het^1oxy$ or $Het^2oxy$, aryl, $C_{1-6}$alkyl, $Het^1C_{1-4}$alkyl, $Het^1oxyC_{1-4}$alkyl, $Het^2 C_{1-4}$alkyl, $Het^2oxyC_{1-4}$alkyl, $arylC_{1-4}$alkyl, $aryloxyC_{1-4}$alkyl or $aminoC_{1-4}$alkyl;
wherein each of the amino groups in the definition of $R_6$ may optionally be substituted with one or more substituents selected from $C_{1-4}$alkyl, $C_{1-4}$alkylcarbonyl, $C_{1-4}$alkyloxycarbonyl, aryl, arylcarbonyl, aryloxycarbonyl, $Het^1$, $Het^2$, $arylC_{1-4}$alkyl, $Het^1C_{1-4}$alkyl and $Het^2C_{1-4}$alkyl; and
$R_5$ and -A-$R_6$ taken together with the nitrogen atom to which they are attached may also form $Het^1$ wherein $Het^1$ is substituted by at least an oxo group.

11. The method of claim 1, wherein:
$R_1$ is $Het^2$ or $Het^2C_{1-6}$alkyl; wherein said $Het^2$ is an aromatic heterocycle having at least one heteroatom each independently selected from nitrogen, oxygen and sulfur; and L is —C(=O)—, —O—C(=O)— or —O—$C_{1-6}$alkyl-C(=O)—.

12. The method of claim 1, wherein:
$R_1$ is $Het^2$ or $Het^2C_{1-6}$alkyl; wherein said $Het^2$ is an aromatic heterocycle having at least two heteroatom each independently selected from nitrogen, oxygen and sulfur; and L is —C(=O)—, —O—C(=O)— or —O—$C_{1-6}$alkyl-C(=O)—.

13. The method of claim 1, wherein:
A is $C_{1-6}$alkanediyl or —C(=O)—;
$R_5$ is hydrogen or methyl; and
$R_6$ is $C_{1-6}$alkyloxy, $Het^1$, $Het^2$, amino or amino$C_{1-6}$alkyl; wherein each amino optionally may be mono- or disubstituted where the substituents are each independently selected from $C_{1-4}$alkyl, aryl, $arylC_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl.

14. The method of claim 1, wherein:
$R_1$ is $Het^2$ or $Het^2C_{1-6}$alkyl; wherein said $Het^2$ is an aromatic heterocycle having at least one heteroatom each independently selected from nitrogen, oxygen and sulfur;
L is —C(=O)—, —O—C(=O)— or —O—$C_{1-6}$alkyl-C(=O)—;
A is $C_{1-6}$alkanediyl or —C(=O)—;
$R_5$ is hydrogen or methyl; and
$R_6$ is $C_{1-6}$alkyloxy, $Het^1$, $Het^2$, amino or amino$C_{1-6}$alkyl; wherein each amino optionally may be mono- or disubstituted, where the substituents are each independently selected from $C_{1-4}$alkyl, aryl, $arylC_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl.

15. The method of claim 1, wherein:
$R_1$ is 2-thiazolylmethyl-; and L is —O—C(=O)—.

16. The method of claim 1, wherein:
$R_5$ is hydrogen; A is —C(=O)—; and
$R_6$ is $Het^2$; wherein said $Het^2$ contains 5 or 6 ring members and one heteroatom selected from nitrogen, oxygen and sulfur.

17. The method of claim 1, wherein:
$R_1$ is $Het^1$, having 8 ring members and two heteroatoms each independently selected from nitrogen, oxygen and sulfur;
L is —O—C(=O)—;
$R_5$ is hydrogen or methyl;
A is —C(=O)— or $C_{1-6}$alkanediyl; and
$R_6$ is optionally mono- or disubstituted amino$C_{1-4}$alkyl, $Het^1$, $Het^2$; wherein said $Het^2$ contains 5 or 6 ring members and one heteroatom selected from nitrogen, oxygen and sulfur; wherein the amino substituents are each independently selected from $C_{1-4}$alkyl, aryl, aryl$C_{1-4}$alkyl, $C_{3-7}$cycloalkyl, $C_{3-7}$cycloalkyl$C_{1-4}$alkyl, $Het^1$, $Het^2$, $Het^1C_{1-4}$alkyl and $Het^2C_{1-4}$alkyl.

* * * * *